(12) United States Patent
Shirazipour et al.

(10) Patent No.: US 11,681,970 B2
(45) Date of Patent: Jun. 20, 2023

(54) AUTOMATED AUGMENTED REALITY RENDERING PLATFORM FOR PROVIDING REMOTE EXPERT ASSISTANCE

(71) Applicant: TELEFONAKTIEBOLAGET LM ERICSSON (PUBL), Stockholm (SE)

(72) Inventors: Meral Shirazipour, Santa Clara, CA (US); Julien Forgeat, San Jose, CA (US); Alvin Jude Hari Haran, Sundbyberg (SE); Per Karlsson, Los Gatos, CA (US)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 0 days.

(21) Appl. No.: 17/051,876

(22) PCT Filed: Apr. 27, 2019

(86) PCT No.: PCT/IB2019/053465
§ 371 (c)(1),
(2) Date: Oct. 30, 2020

(87) PCT Pub. No.: WO2019/211713
PCT Pub. Date: Nov. 7, 2019

(65) Prior Publication Data
US 2021/0192413 A1 Jun. 24, 2021

Related U.S. Application Data

(60) Provisional application No. 62/664,774, filed on Apr. 30, 2018.

(51) Int. Cl.
*G06Q 10/00* (2023.01)
*G06Q 10/0639* (2023.01)
(Continued)

(52) U.S. Cl.
CPC ....... *G06Q 10/06393* (2013.01); *G06N 20/00* (2019.01); *G06Q 10/06311* (2013.01);
(Continued)

(58) Field of Classification Search
CPC .............. G06N 20/00; G06Q 10/06311; A61B 2090/365; G05B 2219/32014; G06F 3/011; G06F 2111/18
See application file for complete search history.

(56) References Cited

U.S. PATENT DOCUMENTS

| | | | |
|---|---|---|---|
| 11,250,947 B2 * | 2/2022 | Divine | G16H 40/20 |
| 2002/0067372 A1 * | 6/2002 | Friedrich | G05B 19/41875 |
| | | | 715/753 |

(Continued)

FOREIGN PATENT DOCUMENTS

| | | |
|---|---|---|
| DE | 102015106470 A | 10/2016 |
| WO | 2017120288 A | 7/2017 |

OTHER PUBLICATIONS

Bleser G, Damen D, Behera A, et al. Cognitive Learning, Monitoring and Assistance of Industrial Workflows Using Egocentric Sensor Networks. PLoS One. 2015;10(6):e0127769. Published Jun. 30, 2015. doi:10.1371/journal.pone.0127769 (Year: 2015).*

(Continued)

*Primary Examiner* — Rutao Wu
*Assistant Examiner* — Tyrone E Singletary

(57) ABSTRACT

A scheme (300) for facilitating automated AR-based rendering with respect to expert guidance or assistance provided in a connected work environment based on contextualization is disclosed. In one aspect, a method comprises a worker (102) requiring assistance with respect to a given task generating (302) one or more suitable queries. Responsive thereto, real-time context data is gathered (304), which may comprise data relating to the work environment. A
(Continued)

remote expert (118) may generate (306) appropriate guidance relevant to the task and assistance query, which may be rendered as AR content (308) for worker consumption by using an AR rendering module (112). The worker (102) consumes or uses the AR content for performing (310) an action with respect to the task. The performance of the worker (102) may be used as a measure to improve the AR rendering in automated fashion (312, 314) using one or more machine learning modules (114).

18 Claims, 14 Drawing Sheets

(51) Int. Cl.
*G06N 20/00* (2019.01)
*G06Q 10/0631* (2023.01)
*G06T 19/00* (2011.01)
*A61B 90/00* (2016.01)
*G06F 3/01* (2006.01)
*G06F 111/18* (2020.01)

(52) U.S. Cl.
CPC ...... *G06T 19/006* (2013.01); *A61B 2090/365* (2016.02); *G05B 2219/32014* (2013.01); *G06F 3/011* (2013.01); *G06F 2111/18* (2020.01)

(56) References Cited

U.S. PATENT DOCUMENTS

| | | | |
|---|---|---|---|
| 2011/0115816 A1* | 5/2011 | Brackney | H05B 47/10 |
| | | | 700/295 |
| 2012/0206323 A1* | 8/2012 | Osterhout | G06Q 30/02 |
| | | | 345/8 |
| 2012/0212400 A1 | 8/2012 | Border et al. | |
| 2013/0278631 A1* | 10/2013 | Border | G06Q 30/02 |
| | | | 345/633 |
| 2014/0204190 A1* | 7/2014 | Rosenblatt, III | G16H 70/20 |
| | | | 705/2 |
| 2015/0192774 A1 | 7/2015 | Watanabe et al. | |
| 2015/0339453 A1* | 11/2015 | Richards | G16H 40/67 |
| | | | 345/633 |
| 2016/0015470 A1 | 1/2016 | Border | |
| 2016/0225192 A1 | 8/2016 | Jones et al. | |
| 2016/0269631 A1* | 9/2016 | Jiang | G09B 5/02 |
| 2018/0053351 A1 | 2/2018 | Anderson | |
| 2018/0165854 A1* | 6/2018 | Du | G06T 11/00 |
| 2020/0130178 A1* | 4/2020 | Colasanto | G05B 19/4155 |
| 2020/0225655 A1* | 7/2020 | Cella | G05B 23/024 |
| 2020/0404100 A1* | 12/2020 | Amir | H04L 65/401 |

OTHER PUBLICATIONS

P. Fraga-Lamas, T. M. FernáNdez-CaraméS, Ó. Blanco-Novoa and M. A. Vilar-Montesinos, "A Review on Industrial Augmented Reality Systems for the Industry 4.0 Shipyard," in IEEE Access, vol. 6, pp. 13358-13375, 2018 (Year: 2018).*

"Industrial internet of things (IIoT)," IoT Agenda, posted by Margaret Rouse, retrieved at http://internetofthingsagenda.techtarget.com/definition/Industrial-Internet-of-Things-IIoT on Oct. 30, 2020.

Long H., "The new normal: 4 job changes by the time you're 32", Money at CNN, Apr. 12, 2016, retrieved at http://money.cnn.com/2016/04/12/news/economy/millennials-change-jobs-frequently/index.html on Jan. 5, 2019.

Gurevich P., et al., "TeleAdvisor: A Versatile Augmented Reality Tool for Remote Assistance", ACM, May 2012, pp. 619-622.

Sodhi R.S., et al., "BeThere: 3D mobile collaboration with spatial input", In Proceedings of the SIGCHI Conference on Human Factors in Computing Systems, CHI 2013: Changing Perspectives, Paris, France, Apr. 2013, pp. 179-188.

Hadar E., et al., "Hybrid remote expert-an emerging pattern of industrial remote support", CAiSE 2017 Forum and Doctoral Consortium Papers, pp. 33-40, 2017.

Kleinman J, et al., "Augmented Reality Glasses: What You Can Buy Now (or Soon)", Tom's Guide, Feb. 14, 2018, retrieved at https://www.tomsguide.com/us/best-ar-glasses,review-2804.html on Jan. 5, 2019.

Liu Y., et al., "Content-aware modeling and enhancing user experience in cloud mobile rendering and streaming", IEEE Journal on Emerging and Selected Topics in Circuits and Systems, vol. 4, No. 1, Mar. 2014, pp. 43-56.

P. Vávra, et al., "Recent Development of Augmented Reality in Surgery: A Review", Journal of Healthcare Engineering, vol. 2017, Jan. 1, 2017, pp. 1-9.

Chen L., et al., "Recent Developments and Future Challenges in Medical Mixed Reality," 2017 IEEE International Symposium on Mixed and Augmented Reality (ISMAR), Aug. 3, 2017, pp. 1-13.

A. Y. C. Nee, et al., "Augmented reality applications in design and manufacturing", CIRP Annals—Manufacturing Technology, vol. 61, No. 2, Jan. 1, 2012 (Jan. 1, 2012), pp. 657-679.

Raghavan V., et al., "Interactive Evaluation of Assembly Sequences Using Augmented Reality", IEEE Transactions on Robotics and Automation, IEEE Inc, New York, US, vol. 15, No. 3, Jun. 1, 1999, pp. 435-449.

* cited by examiner

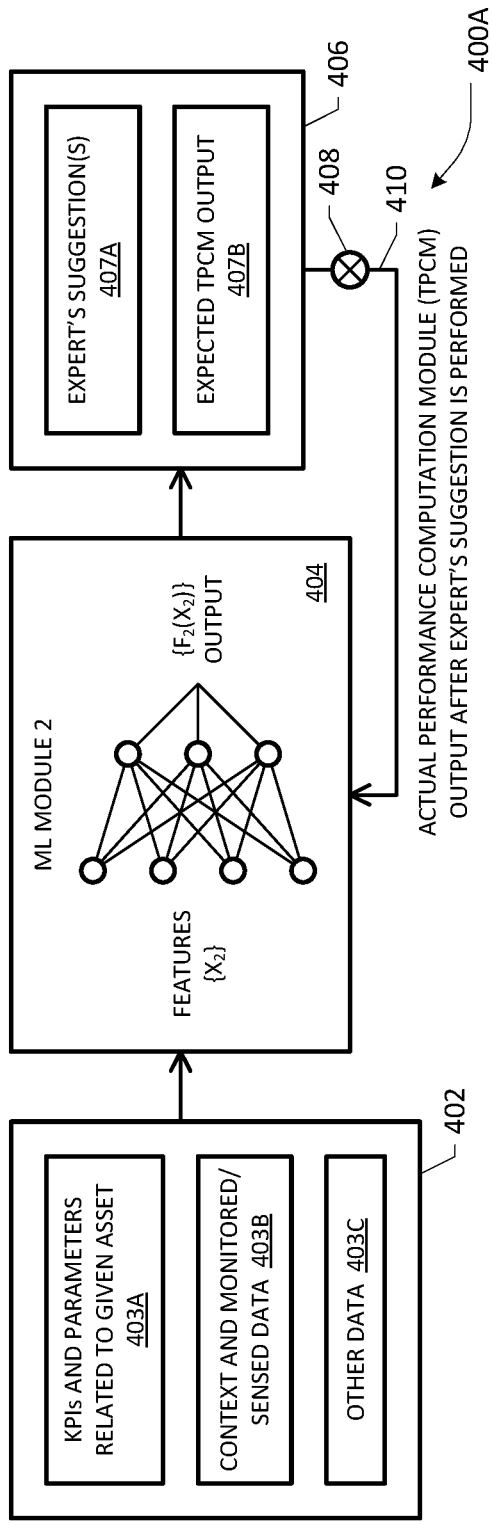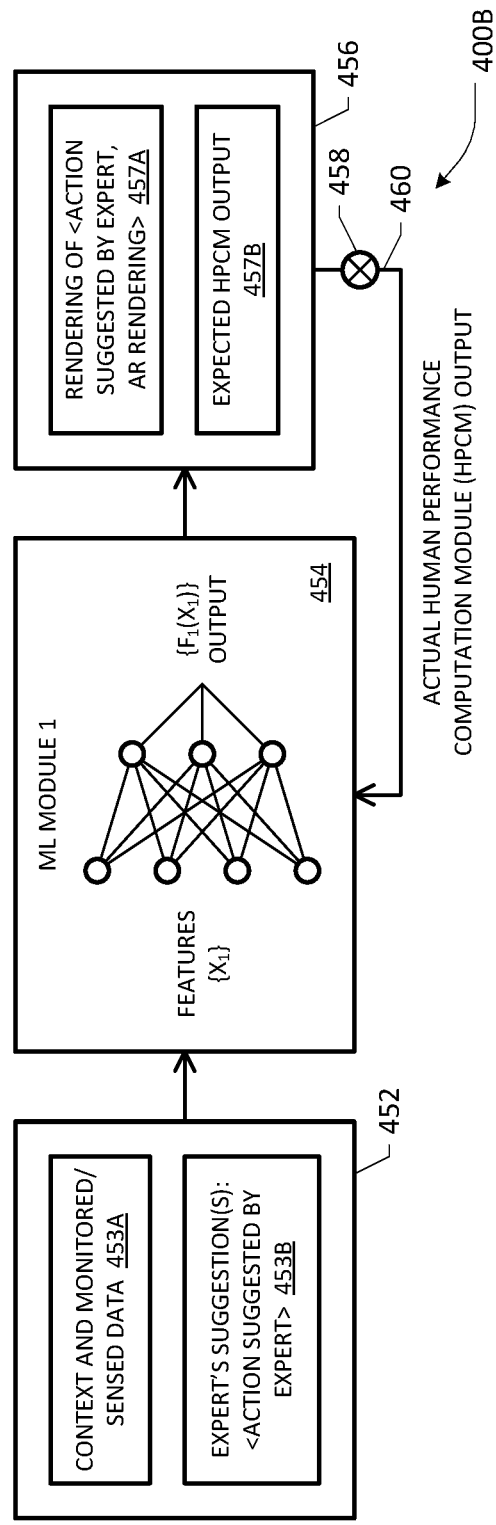
FIG. 4A
FIG. 4B

TRAINING THE FIRST ML MODULE RESPONSIVE TO FEEDBACK RECEIVED FROM A HUMAN PERFORMANCE COMPUTATION MODULE (HPCM) CONFIGURED TO MEASURE, OBTAIN OR OTHERWISE DETERMINE ONE OR MORE PERFORMANCE/RENDITION METRICS, E.G., (I) ACCURACY OF THE CONSTRUCTION OF THE DIGITAL REPRESENTATION OF THE RESPONSE ACTION; (II) INDICATION OF PERFORMANCE QUALITY IN EXECUTING THE RESPONSE ACTION BY THE AT LEAST ONE REQUESTER WITH RESPECT TO THE TASK, ETC.
— 512

FACILITATING GENERATION OF ONE OR MORE GUIDANCE MESSAGES BASED AT LEAST IN PART UPON FEEDBACK RECEIVED FROM A SECOND MACHINE LEARNING (ML) MODULE CONFIGURED TO PROVIDE FEEDBACK TO THE REMOTE EXPERT(S) WITH RESPECT TO TASK PERFORMANCE AND COMPLETION DATA PROVIDED BY A TASK PERFORMANCE COMPUTATION MODULE (TPCM)
— 514

INTERACTING WITH THE AT LEAST ONE REQUESTER VIA A QUERY-RESPONSE MECHANISM TO IMPROVE THE DIGITAL REPRESENTATION OF THE RESPONSE ACTION FOR FACILITATING A MORE ACCURATE AR RENDERING
— 516

TRAINING AT LEAST ONE OF THE FIRST ML MODULE AND THE SECOND ML MODULE USING A SIMULATED CONTEXTUAL SETTING WITH RESPECT TO THE TASK, THE TRAINING TAKING PLACE PRIOR TO PROVIDING ANY GUIDANCE MESSAGES TO THE AT LEAST ONE REQUESTER
— 518

500E

FIG. 5E

AUTOMATED AUGMENTED REALITY RENDERING PLATFORM FOR PROVIDING REMOTE EXPERT ASSISTANCE

PRIORITY AND CROSS-REFERENCE TO RELATED APPLICATION(S)

This patent application claims priority based upon the following prior United States provisional patent application(s): (i) "AUTOMATED AUGMENTED REALITY RENDERING PLATFORM FOR INDUSTRIAL EXPERT ASSISTANCE," Application No.: 62/664,774, filed Apr. 30, 2018, in the name(s) of Meral Shirazipour, Per Karlsson, Alvin Jude Hari Haran and Julien Forgeat; each of which is hereby incorporated by reference in its entirety.

TECHNICAL FIELD

The present disclosure generally relates to communication networks. More particularly, and not by way of any limitation, the present disclosure is directed to a system, method, apparatus and associated computer readable media for facilitating an automated augmented reality (AR) rendering platform configured to provide remote expert assistance in a networked environment.

BACKGROUND

Increasingly, augmented reality (AR) and virtual reality (VR) are becoming more than gaming environments, with companies finding enterprise potential in the technology in a host of applications. One of the goals of the industry is to replace conventional user interfaces such as keyboards, displays, etc. with new paradigms for human-machine communication and collaboration, thereby facilitating a major shift in user engagement in AR/VR environments. Accordingly, the enterprise potential of AR/VR technology continues to grow as companies are constantly exploring new use cases beyond pilot or "one-off" applications.

Mixed reality (MR) represents a further advance where both AR and real world environments may be merged in additional enhancements to provide richer user experiences. As the advances in AR/VR/MR technology continue to grow apace, interest in applying the technology in a much broader range of use case scenarios has also grown concomitantly. In particular, the applicability of AR in business and industrial settings is gaining momentum in aspects such as ubiquitous computing, Industrial Internet of Things (IIoT) and artificial intelligence (AI) interaction. Also known as the Industrial Internet (e.g., Industry 4.0), IIoT involves the use of IoT technologies in manufacturing, and may incorporate machine learning and Big Data technology, harnessing sensor data, machine-to-machine (M2M) communications and automation technologies that may be implemented in an industrial setting.

IIoT spans various industrial sectors such as healthcare, transport, smart cities, manufacturing and energy, just to name a few. In these industries and specially manufacturing, where the quality of the work depends on a well workforce, the industry is also facing a new challenging reality, that of the constant churn in workforce. Current trends appear to suggest that millennial and post-millennial workers will switch jobs a lot more often (e.g., every three years), creating massive employee turnover and the need to deal with inexperienced workers. To address such needs as well as leverage the opportunities brought forth by IIoT, especially in the Next-generation (5th generation or 5G) mobile networks, the application of AR for providing remote worker assistance is being heavily investigated. Whereas advances relative to providing remote assistance using AR in connected work environments continue to grow apace, several lacunae remain, thereby requiring further innovation as will be set forth hereinbelow.

SUMMARY

The present patent disclosure is broadly directed to systems, methods, apparatuses, devices, and associated non-transitory computer-readable media or computer program products for facilitating automated AR-based rendering with respect to expert guidance provided in a connected work environment based on contextualization. In one aspect, an embodiment of a remote assistance rendering method may comprise, inter alia, a worker (or its agent) requiring assistance with respect to a given task generating one or more suitable queries. Responsive thereto, real-time context data is gathered, which may comprise various pieces of data relating to the work environment, including, e.g., object identification, spatial mapping data, task data and the worker data, etc. At least in some arrangements, the work environment may form an integrated ambient workspace that blends physical, virtual and sensor-integrated ambient/proximal spaces in which the worker and the task are disposed. A remote expert (e.g., a "helper") may generate appropriate guidance relevant to the task assistance query, which may be rendered as AR content for worker consumption by using an AR rendering module. The worker consumes or uses the AR content for performing a response action with respect to the task, which may involve commission or omission of an act. In one embodiment, guidance generation and AR rendering (i.e., creating appropriately contextualized AR content corresponding to the guidance) may be modulated by using trainable machine learning (ML)-based models with respect to such processes. In one embodiment, measurements relative to the rendering, human/task performance, etc., may be obtained, which may be fed back to improve the ML models that in turn can be configured to enhance the guidance generation and AR rendering processes. In one implementation, an embodiment of the foregoing scheme may be performed in parallel for multiple workers and/or tasks (e.g., in a multithreaded fashion).

In another aspect, an embodiment of a method comprises, inter alia, receiving, from a remote expert, one or more guidance messages generated responsive to an assistance request provided by at least one requester (e.g., worker, or its agent/proxy, which can be either machine or another human) with respect to a task to be performed by the at least one requester in a contextual setting. Responsive to the one or more guidance messages from the remote expert, a digital representation of a response may be constructed (i.e., "rendered") with respect to an action to be taken by the at least one requester regarding the task, wherein the digital representation is based on contextual data obtained with respect to the at least one requester and the task. The digital representation of the response is provided to the at least one requester for presentation via an AR overlay in a UE device operated by the at least one requester. In one variation, the construction of the digital representation is facilitated based at least in part upon rendering output received from a first ML module configured to automatically generate AR rendering of remote expert guidance messages in a trainable manner. In one variation, the first ML module is trained responsive to feedback received from a human performance computation module (HPCM) configured to obtain at least one of: (i) accuracy of the construction of the digital representation of the response; and (ii) indication of performance quality in executing the response by the at least one requester with respect to the task. In a further variation, guidance messages generated by the remote expert are facilitated based at least in part upon feedback received from a second ML module configured to provide feedback to the remote expert with respect to task performance and completion data provided by a task performance computation module (TPCM). In a further variation, at least one of the first ML module and the second ML module may be trained in a simulated contextual setting with respect to the task.

According to certain embodiments, a network node or element for providing AR-based assistance is disclosed, which includes, inter alia, memory operable to store instructions and processing circuitry operable to execute the instructions to cause the node to receive a request for task assistance of and/or from a first user associated with an AR device. Context data may be gathered in real-time and in response to receiving the request for assistance with the task. A recommendation identifying the performance of an action associated with the task is received. Based on the context data, a machine learning model is used to generate an AR rendering of the action identified in the recommendation. The rendering of the action is transmitted to the AR device associated with the first user. Information associated with a performance of the action by the first user is received, and the ML model is updated based on the feedback associated with the performance of the action by the first user.

In one variation, an example process of expert assistance may be triggered by a worker or another entity on behalf of and/or in combination with the worker, wherein such entity may comprise a machine or proxy that may be configured to generate requests based on supervision of the worker performing a task.

In a still further aspect, an embodiment of a system, apparatus, or computer platform is disclosed which comprises, inter alia, suitable hardware such as processors and persistent memory having program instructions for executing an embodiment of one or more methods set forth herein.

In still further aspects, one or more embodiments of a non-transitory computer-readable medium or distributed media containing computer-executable program instructions or code portions stored thereon are disclosed for performing one or more embodiments of the methods of the present invention when executed by a processor entity of a network node, apparatus, system, network element, workstation, server, and the like, mutatis mutandis. Further features of the various embodiments are as claimed in the dependent claims.

Example embodiments of the present patent disclosure may provide one or more of the following technical advantages. For example, a technical advantage may be that certain embodiments provide a platform that enables the use of AR/MR in conjunction with IIoT technologies to assist less experienced workers by one or more remote experts. As a result, the platform may allow high quality manufacturing production that reduces errors and provides other advantages (e.g., cost efficiencies in terms of lower capital/operating expenditures (CapEx/OpEx)). Still another advantage may be that an example platform relies on 5G connectivity and edge compute architecture for machine learning techniques to operate as required in real-time, thereby advantageously operating within the constraints of efficient bandwidth utilization and optimization in an AR-supported network.

A still further technical advantage may be that certain embodiments may provide an automated method for learning the best AR rendering for various specific tasks with automated user testing. As another example, certain embodiments may present an online method that connects to an existing remote expert assistance platform to train models so as to be able to perform as well as all the experts involved in the process. That is, the models may outperform individual human experts as the models are trained from data from all of the experts. As still another example, a technical advantage may be that the machine learning modules set forth herein can further help human remote experts with providing the best guidance to a worker based on previous learning experiences for that context, which may include the task and environmental conditions as well as specific worker information over a period of time (e.g., historical contextualization).

Generally, all terms used herein are to be interpreted according to their ordinary meaning in the relevant technical field, unless a different meaning is clearly given and/or is implied from the context in which it is used within the present patent application. All references to a/an/the element, apparatus, component, means, step, etc. are to be interpreted openly as referring to at least one instance of the element, apparatus, component, means, step, etc., unless explicitly stated otherwise. As will be seen below, the steps of any methods disclosed herein do not have to be performed in the exact order disclosed, unless a step is explicitly described as following or preceding another step and/or where it is implicit that a step must follow or precede another step. Any feature of any of the embodiments disclosed herein may be applied to any other embodiment, wherever appropriate. Likewise, any advantage of any of the embodiments may apply to any other embodiments, and vice versa. Other objectives, features and advantages of the disclosed embodiments will be apparent from the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to affect such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 4A and 4B depict block diagrams of machine learning (ML) modules that may be used in association with an ARRA platform according to one or more embodiments of the present patent disclosure;

FIGS. 5A-5E depict flowcharts of various blocks, steps and/or acts that may be (re)combined in one or more arrangements, with or without additional flowcharts of the present disclosure, for effectuating further aspects of a remote assistance platform according to one or more embodiments of the present patent disclosure;

DETAILED DESCRIPTION

Figure 1:
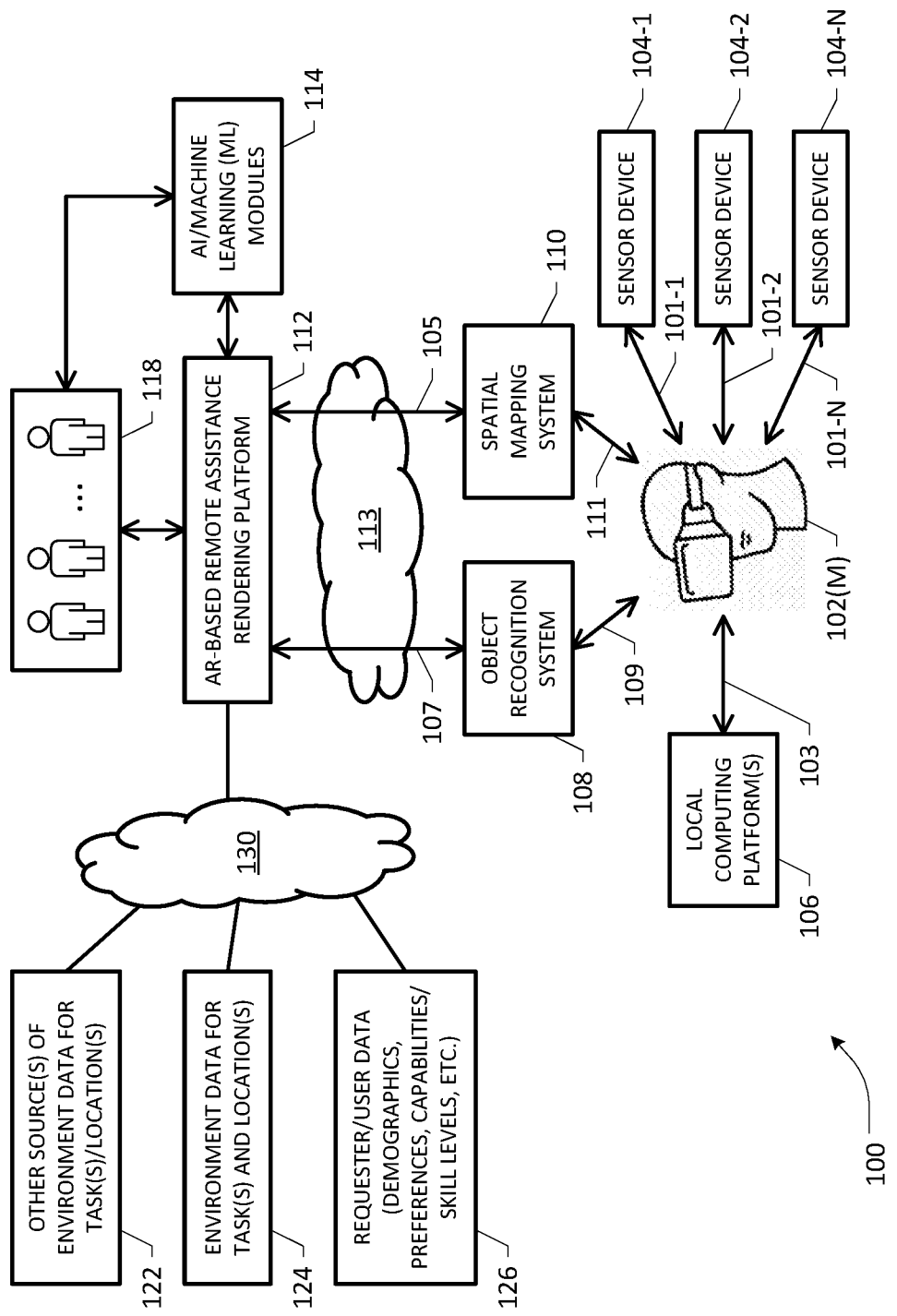
FIG. 1 depicts an example network environment including an AR-based remote assistance (ARRA) platform in accordance with an embodiment of the present patent disclosure.

In the following description, numerous specific details are set forth with respect to one or more embodiments of the present patent disclosure. However, it should be understood that one or more embodiments may be practiced without such specific details. In other instances, well-known circuits, subsystems, components, structures and techniques have not been shown in detail in order not to obscure the understanding of the example embodiments. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an element, component or module may be configured to perform a function if the element is capable of performing or otherwise structurally arranged or programmed under suitable executable code to perform that function.

As used herein, a network element, platform or node may be comprised of one or more pieces of service network equipment, including hardware and software that communicatively interconnects other equipment on a network (e.g., other network elements, end stations, etc.), and is adapted to host one or more applications or services with respect to facilitating an automated AR-based remote assistance rendering scheme according to the teachings herein. As such, some network elements may be disposed in a cellular wireless or satellite telecommunications network, or a broadband wireline network, whereas other network elements may be disposed in a public packet-switched network infrastructure (e.g., the Internet or worldwide web, also sometimes referred to as the "cloud"), private packet-switched network infrastructures such as Intranets and enterprise networks, as well as service provider network infrastructures, any of which may span or involve a variety of access networks, backhaul networks and core networks in a hierarchical arrangement. In still further arrangements, one or more network elements may be disposed in cloud-based platforms or data centers having suitable equipment running virtualized functions or applications relative to one or more processes set forth hereinbelow.

Example end stations and client devices (broadly referred to as User Equipment or UE devices) may comprise any device configured to generate assistance queries and consume AR content containing remote guidance obtained via one or more suitable access networks or edge network arrangements based on a variety of access technologies, standards and protocols. Accordingly, example UE devices may comprise smartphones, multimedia/video phones, mobile/wireless user equipment, portable media players, smart wearables such as smart watches, goggles, digital gloves, portable laptops, netbooks, palm tops, tablets, phablets, mobile phones, IoT devices and sensors, connected vehicles (manual and/or autonomous), and the like, as well as networked or local computing devices including AR/MR/VR gear. In a further variation, some UE devices or subscriber end stations may also access or consume AR content and remote assistance services provided on virtual private networks (VPNs) overbid on (e.g., tunneled through) the Internet.

One or more embodiments of the present patent disclosure may be implemented using different combinations of software, firmware, and/or hardware in one or more modules suitably programmed and/or configured. Thus, one or more of the techniques shown in the Figures (e.g., flowcharts) may be implemented using code and data stored and executed on one or more electronic devices or nodes (e.g., a UE device or end station, a network element, etc.). Such electronic devices may store and communicate (internally and/or with other electronic devices over a network) code and data using computer-readable media, such as non-transitory computer-readable storage media (e.g., magnetic disks, optical disks, random access memory, read-only memory, flash memory devices, phase-change memory, etc.), transitory computer-readable transmission media (e.g., electrical, optical, acoustical or other form of propagated signals—such as carrier waves, infrared signals, digital signals), etc. In addition, such network elements may typically include a set of one or more processors coupled to one or more other components, such as one or more storage devices (e.g., non-transitory machine-readable storage media) as well as storage database(s), user input/output devices (e.g., a keyboard, a touch screen, a pointing device, and/or a display), and network connections for effectuating signaling and/or bearer media transmission. The coupling of the set of processors and other components may be typically through one or more buses and bridges (also termed as bus controllers), arranged in any known (e.g., symmetric/shared multiprocessing) or heretofore unknown architectures. Thus, the storage device or component of a given electronic device or network element may be configured to store code and/or data for execution on one or more processors of that element, node or electronic device for purposes of implementing one or more techniques of the present disclosure.

Referring now to the drawings and more particularly to FIG. 1, depicted therein is an example network environment 100 including an automated AR-based remote assistance rendering (ARRA) platform according to one or more embodiments of the present patent application. It should be appreciated that the terms "augmented reality" or "AR" and "mixed reality" or "MR" may be used somewhat interchangeably for purposes of an embodiment of the present invention. Further, where only "AR" or "MR" is mentioned, it will be realized that these terms represent both AR and MR, cumulatively or otherwise. In the context of the present patent disclosure, AR-based remote assistance is a technology where a real world work environment is augmented by a variety of virtual or digital representations rendered with respect to any guidance or assistance provided by a first type of entities (usually experts or helpers) to a second type of entities (usually less skilled workers) located in the real world work environment in a highly contextualized manner. Accordingly, the real world and its physical objects, images, senses, sounds, and other tangible quantities in a physical/work environment that is viewed, sensed, heard, or otherwise perceived or experienced by a user (herein a "worker" or "requester" and/or its agent/proxy, either in association with, on behalf of or independent of the worker, that seeks to obtain assistance, either alone on in conjunction with other workers or requesters, with respect to at least a portion of a task or project to be performed) using a suitable display/computing device and other related hardware is augmented or supplemented with or by virtual objects or other computer-generated sensory input such as sound, video, graphics, olfactory and tactile sensory data, as well as suitable location data in some cases, relating to actions, instructions, suggestions, etc. provided by one or more experts, that are rendered in a personalized or individualized basis based on the contextual data relating to the worker, task at hand as well as the work environment.

Skilled artisans will recognize upon reference hereto that a work environment for purposes of the present patent disclosure may comprise any commercial, residential, industrial, manufacturing, medical/surgical or any other organizational setting where one set of users may require and obtain AR-based assistance from more skilled personnel or entities that may be located nearby and/or in remote locations. In a general sense, AR may be an overlay of content on the real world work environment, but that content may or may not be anchored to or part of the physical view or its objects. More broadly, some embodiments of the present invention may treat mixed reality (MR) as a mix of AR and VR (which typically involves a completely simulated environment), sometimes also referred to as "hybrid reality" that involves a merging of real and virtual worlds to produce an enhanced work environment and associated visualization where physical and computer-generated objects, sounds, images, etc. (collectively, "entities") may coexist and even interact in real-time. In other words, MR can be considered an overlay of synthetic entities or content on the real world environment that are anchored to and interact with the physical objects/entities therein in some meaningful fashion. Thus, in an MR environment, an embodiment may not only allow for the merger of digital objects within a real world scenario but also facilitate extra real life textural, tactile, olfactory, visual, aural, or other sensory feedback such as "depth", "surfaces", "material type", etc.

By way of illustration, the network architecture 100 of FIG. 1 exemplifies one or more workers 102(M) each operating suitable AR/MR devices and disposed in an example work environment with respect to performing a job, task or project therein for which assistance may be desired. It will be apparent that such tasks, jobs or projects may involve, without limitation, myriad types of hardware, equipment, tools, instrumentation, apparatuses, devices, software, etc., in any number of combinations or sub-combinations, which may be deployed in virtually any work environment or setting, e.g., industrial, residential, manufacturing, etc., as noted above. Typical UE devices may be operative with advanced AR/MR technologies including, e.g., computer/machine vision and object recognition, in addition to inter-operating with various sensory devices 104-1 to 104-N, at least some of which may be integrated within respective UE devices in an embodiment. Where such sensory devices may be provided as separate entities or elements, they may communicate with the AR/MR devices using suitable wired and/or wireless communications technologies, e.g., optical, radio, Bluetooth, etc., for generating, receiving and/or transmitting myriad types of sensory data and associated control signaling, via applicable communication paths 101-1 to 101-N. Example sensory devices 104-1 to 104-N may include but not be limited to cameras, microphones, accelerometers, gyroscopes, Global Positioning System (GPS) locators, inertial sensors, light/brightness sensors, touch sensors, mood sensors, temperature sensors, direction/orientation sensors, pressure sensors, gesture sensors/controllers, optical scanners, near-field communications (NFC) devices, head/hand movement detectors, ocular movement trackers, and directional sensors such as solid-state compasses, etc., as well as wearable devices comprising health/exercise monitors and biometric identification devices, and so on. Further, at least a subset of sensors may be provided as part of an Industrial Internet of Things (IIoT) architecture associated with the work environment in which workers 102(M) are disposed. In general, sensor devices 104-1 to 104-N may therefore be configured, at least in some arrangements, to generate, monitor, sense, provide, measure, obtain, or otherwise determine various pieces of data or information with respect to not only the individual worker(s) but also regarding the status of the hardware, equipment, tools, instrumentation, apparatuses, devices, software, etc. involved in the task. In some arrangements, at least some sensors or sensor-based modules may also be configured to provide, generate, or otherwise obtain data relating to physical working conditions, quality of workers' performance, progression of a task, as well as suitable Key Performance Indicators (KPIs) relative to the tasks, etc.

According to some embodiments, one or more local computing platforms or devices 106 (e.g., including hardware, operating system software/firmware and applications) may also be provided (optionally or otherwise), which may be operated by workers 102(M) in conjunction with or independent of respective AR/MR devices associated therewith. For example, such local computing devices 106 may be configured to communicate or interoperate with the users' AR/MR devices via one or more communication paths 103, wherein the local computing devices 106 may represent any number and/or type of desktop computers, laptops, mobile/smartphones, tablets/phablets, holographic computers, etc. Collectively, the local computing hardware/software devices 106, user AR/MR devices and associated sensory devices 104-1 to 104-N may be considered as an exemplary representation of an AR/MR-enhanced work environment wherein local workers 102(M) may be engaged in a number of tasks, jobs, processes or projects, etc., with respect to which appropriate requests or queries for assistance may be generated to an AR-based assistance rendering platform 112 as will be described in detail further below. In one arrangement, example network architecture 100 may include or interface with a plurality of such local work environments depending on scale (e.g., tens, hundreds or more).

In an example work environment, workers 102(M) may be equipped with devices such as head-mounted display (HMD) devices operative as part of the AR/MR equipment, which may be paired with a helmet or a harness adjustable to the worker and may employ sensors for six degrees-of-freedom monitoring that allows alignment of virtual information to the physical world perceived in a field of view (FOV) and adjust accordingly with the user's head and/or eye movements. Example AR/MR devices may also comprise devices resembling eyewear or goggles that include cameras to intercept the real world view and display an augmented view through an eye piece or as a projected view in front of the user. Such devices may include but are not limited to equipment such as, e.g., Google Glass, Osterhout Design Group (ODG) R-7/8/9 Smartglasses, Vuzix Blade AR, Magic Leap Lightwear, Optivent Ora-2, Microsoft HoloLens, etc., as well as bionic/haptic gloves or other kinesthetic devices, bionic/electronic contact lenses and virtual retinal displays.

In accordance with the teachings of the present patent disclosure, an Object and sound Recognition System (ORS) 108 and a Spatial Mapping System (SMaS) 110 may be integrated or otherwise co-located with the local work environment, e.g., integrated with local computing devices 106 and/or users' AR/MR equipment. In an alternative or additional embodiment, ORS 108, SMaS 110 or both may be provided as separate network infrastructure elements disposed in an edge/access network servicing a local work environment, communicatively operating therewith using suitable wired/wireless communication paths 109, 111, respectively. In a still further embodiment, ORS 108 and/or SMaS 110 may be implemented as a virtual functionality or appliance in a cloud-based implementation. In one embodiment, irrespective of the specific implementation, ORS 108 may be configured as a system, apparatus or virtual appliance that is operative, depending on available sensors and/or other peripherals associated with an example local work environment and its AR/MR equipment, for collecting information about physical objects, sounds, smells, and other physical/environmental conditions associated with the local work environment (e.g., temperature, ambient noise levels, etc.), collectively referred to herein as "sensory and environmental information". In some example embodiments, AR/MR devices may also include biometrics-based sensors that may be configured to provide suitable personal information that may be used to determine, evaluate or otherwise assess the individual characteristics, conditions, capabilities, etc. of respective workers 102(M). Depending on where an example implementation of ORS is located, the processing of the sensory/environmental data may be effectuated locally on the AR/MR devices, local computing platform(s) 106, or on the network edge/cloud infrastructure where the sensory/environmental data may be transmitted via cellular, WiFi and/or other types of connectivity. Skilled artisans will realize that various known or heretofore unknown techniques may be employed for processing the sensory/environmental data (e.g., image recognition, pattern recognition, machine vision techniques, etc.) so as to identify/recognize the existing physical world objects, images, sounds, environmental conditions, etc. in relation to a real world view seen/perceived via workers' AR/MR equipment and generate real world object identification data with respect to the tasks, jobs, processes or projects engaged by the workers 102(M).

Continuing to refer to FIG. 1, SMaS 110 may be configured as a system, network element, or a cloud-based virtual appliance operative to detect or otherwise identify surfaces and objects in the real world environment perceived in a FOV of a worker's AR/MR equipment. In one example embodiment, SMaS 110 is further operative to map the physical objects, i.e., where they are relative to one another in the FOV. For example, the FOV of a worker may be constantly changing in relation to the head/ocular movement of the worker as well as depending on whether or not the worker is also moving (i.e., walking, running, etc.). Accordingly, SMaS 110 may be configured to dynamically map or remap the physical objects identified in the changing FOV and provide the spatial relationships among the physical objects to the ARRA rendering platform 112. As with ORS 108, one skilled in the art will realize that various known or heretofore unknown techniques may be employed for performing spatial mapping of the physical objects (e.g., using depth/perception sensors, movement sensors, etc.), which data may be dynamically and/or programmatically updated (e.g., based on preconfigured update triggers). Broadly, the SMaS module 110 may be configured to perform spatial mapping of the physical environment in order to understand where the objects are in the real world and how the work environment is laid out (e.g., surfaces and spaces, relative distances and orientations in a 2D/3D view) and provide the spatial mapping data to the ARRA platform 112. Further, depending on where an example implementation of SMaS functionality is located, the processing required for spatial mapping of the physical environment may be effectuated locally on the workers' AR/MR equipment and/or associated local computing platforms 106, or on the network edge/cloud infrastructure. Whether ORS 108 and/or SMaS 110 are co-located with the local work environment or implemented as network nodes in a suitable infrastructure, real world object identification data and/or spatial mapping data may be provided to and received by the ARRA rendering platform 112 via applicable communication network(s) 113 that effectuate suitable communication paths 107, 105, respectively, based on a variety of wired/wireless communication technologies, e.g., cellular technologies (3G/4G/5G or Next Generation), WiFi, Bluetooth, broadband cable, satellite technologies, etc.

In some embodiments of the present invention, the functionalities of ORS 108 and SMaS 110 may also be integrated or otherwise co-located as a single node or module. In general, ORS 108 and SMaS 110 may inter-operate together wherein the coordinates of a real world work environment and the physical objects therein may be derived or generated using a combination of techniques involving computer vision, video tracking, visual odometry, etc. In a first or initial stage, the process may involve detecting various interest points, fiducial markers, or optical flow in the sensed camera images, wherein various feature detection methods such as corner detection, blob detection, edge detection, and other image processing methods may be employed. In a follow-up or second stage, a real world coordinate system and the location/positioning of the physical objects therein may be restored from the data obtained in the first stage, using techniques including but not limited to simultaneous localization and mapping, projective/epipolar geometry, nonlinear optimization, filtering, etc. In an example implementation, AR Markup Language (ARML) may be used to describe the location and appearance of the objects in an AR/MR-enhanced workplace scenario.

Depending on implementation, there may be other sources of data and information relating to the tasks, workers and the workplace, which may be provided via suitable network communications 130 to ARRA platform 112 for purposes of facilitating optimized and/or highly contextualized rendering of assistance or guidance to one or more workers 102(M) responsive to suitable assistance queries generated therefrom. By way of illustration, requester/worker-specific data 126, environmental data of tasks and locations 124 sourced within an organization as well as third-party sources of data relating to tasks and locations 122 may be configured to provide job-specific and/or query-specific data to an embodiment of ARRA platform 112.

As will be set forth in further detail below, one or more experts comprising human experts, artificial intelligence (AI)-based experts, or any combination thereof, collectively referred to as experts 118, may form domain-specific or domain-based knowledge pools that interface with ARRA 112 for providing suitable guidance, supervision, etc. with respect to task-related assistance queries emanating from one or more workers 102(M), which may be rendered in a contextualized manner by ARRA 112. In one embodiment, at least a portion of the various pieces of worker data and environmental/sensory data may be utilized by the experts 118 in generating appropriate answers, suggestions or recommendations and the like, responsive to the task-specific assistance queries. As will be further set forth below, an embodiment of ARRA platform 112 is operative responsive to data from workers 102(M) as well as sensors 104-1 to 104-N, e.g., by way of sensory and real world object identification data, spatial mapping data, among other pieces of information, to generate appropriate digital representations or renderings of the experts' responses to the assistance queries that may be presented to the workers 102(M) via AR/MR equipment in a highly personalized/individualized fashion so as to enable the workers 102(M) to perform the tasks and task-specific guidance actions in an efficient and error-free (or less error-prone) manner. In some example embodiments, such renderings may preferably be executed in real-time or substantially near real-time with respect to the generation of assistance queries. In still further embodiments, the expert guidance generation process and/or AR rendering process may be facilitated and/or enhanced by the use of trainable machine learning (ML)-based modules or AI-based modules, collectively shown trainable modules 114, for refining the overall process based on feedback information received relative to the various aspects of the work environment, task performance, worker performance, etc.

Figure 2:
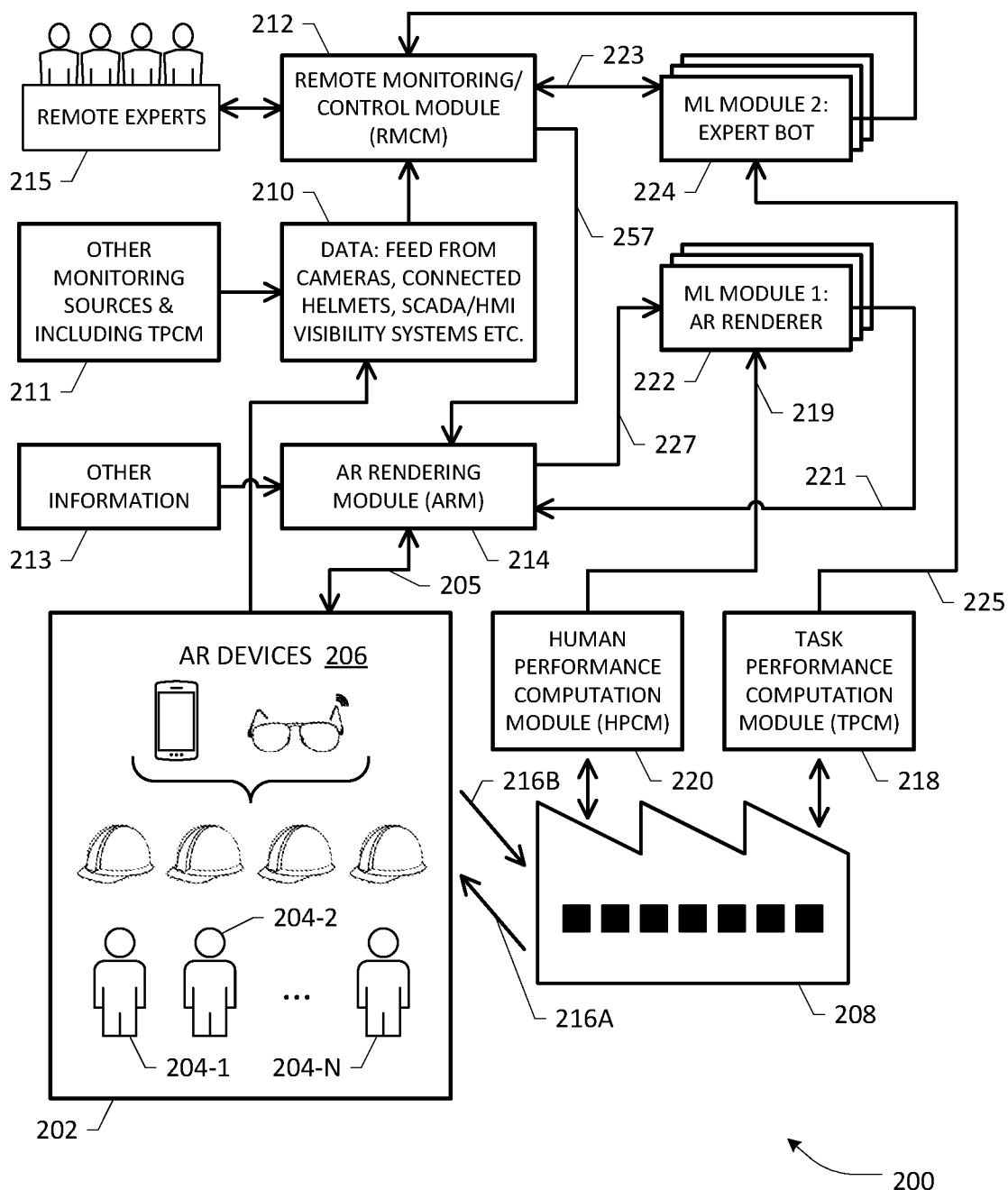
FIG. 2 depicts an architectural arrangement with respect to an implementation of the ARRA platform of FIG. 1 according to an embodiment.

FIG. 2 depicts an exemplary system 200 illustrative of an architectural arrangement involving a plurality of modules that may comprise or be interfaced with a suitable AR rendering platform (e.g., ARRA platform 112 of FIG. 1) for facilitating rendering of assistance between workers 204-1 to 204-N of an environment 208 and one or more experts 215. In some aspects, certain embodiments may include an automated AR rendering platform for providing industrial expert assistance in a remote setting, e.g., where one or more experts may be disposed in a geographically remote location with respect to one or more workers. In some embodiments, the experts may be intra-organizational experts or internal experts that may be locally or remotely based. In some embodiments, the experts may be external or third-party experts, e.g., experts or entities providing "expertise as a service" (EaaS), which may again be disposed in proximal or remote locations with respect to the workers requiring assistance. Accordingly, it should be appreciated that the term "remote assistance" in the context of the present disclosure is not necessarily limited to expert guidance being provided by physically remotely located experts. Rather, whenever an AR/MR-equipped worker requires assistance with respect to a task at hand and generates a query relative thereto to an entity that is configured to generate one or more personalized/contextualized digital representations of expert guidance for AR/MR presentation, regardless of where the expert guidance is emanating from, such assistance may be deemed remote assistance at least for some embodiments. Further, according to certain embodiments, example system architecture 200 may also include at least two ML-based modules for providing additional enhancements with respect to such assistance. Specifically, a first ML module 222 (herein referred to as ML Module 1 or AR-ML module) may automatically improve the AR rendering process by using machine learning to automate user testing. A second ML module 224 (herein referred to as ML Module 2 or Remote Expert-ML (RX-ML) module) may learn from the recommendation of experts and build one or more expert bots (e.g., autonomous programs executing automatically or programmatically in a connected network environment) that may be configured to assist existing experts and eventually replace them for some tasks or serve the experts with a knowledge-base obtained from all other experts. Additional details with respect to such ML modules along with other modules for purposes of some example embodiments will be set forth further below.

Turning attention to data input aspects of the system architecture 200, a data module 210 is representative of various sources of data related to the task(s) being handled by the users 204-1 to 204-N (either in concert or individually). Example data inputs may comprise sensor readings, KPIs, visual, auditory and other data collected from AR gear's sensors and other sensor data (e.g., based on object recognition and spatial mapping mechanisms set forth above in reference to FIG. 1). For example, at least part of the data input may involve data feeds from AR/MR devices, cameras, connected helmets/Head-Up Displays (HUDs), digital gloves, smart wearables, etc., based on appropriate Supervisory Control and Data Acquisition (SCADA) visibility systems and Human-Machine Interface (HMI) systems. Depending on implementation, the actual data may be stored in a distributed or centralized fashion within or outside the system architecture 200. Regardless of data storage distribution, such data may be used at various points and by one or more modules depicted in the system architecture 200, in addition to at least parts of such data being obtained as feedback information from one or more modules as will be described below. By way of illustration, various other contextual/monitoring data as well as feedback data is cumulatively shown as a data feed 211. A Remote Monitoring/Control Module (RMCM) 212 may be configured as an interfacing system between the remote experts 215 and the overall ARRA system architecture 200. In one implementation, one or more experts 215 may be assigned different tasks (e.g., as in a call center) that require further supervision/guidance. For instance, the experts 215 may make recommendations to one or more workers 204-1 to 204-N associated with the work environment 208, comprising a workforce 202 on the field. In some implementations, a single remote expert may assist multiple workers. In other implementations, multiple remote experts may operate in concert to assist a single worker. An AR Rendering Module (ARM or ARRM) 214 is roughly analogous to and/or may comprise at least a portion of the ARRA platform 112 set forth in FIG. 1. In some implementations, the ARM module 214 is operative to receive the expert's recommendation(s), suggestion(s), instruction(s), etc. (collectively "guidance") via suitable message interfacing 257 from RMCM 212 for a given task and/or task-based query. According to one example embodiment, ARM 214 may also be configured to use other information 213 such as, e.g., on the field environment settings, personal data about the worker(s), etc. In addition, ARM 214 may also receive data feeds from AR devices 206 used for object detection and spatial mapping, e.g., via interface 205. Responsive to the guidance messages as well as the foregoing pieces of data, ARM 214 may be configured to render specific AR content (i.e., generate digital representations of actions, etc.) that will help in conveying the expert's recommendation(s) (e.g., generated or otherwise obtained via/from RMCM 212) for presentation to the worker(s) via AR devices 206 in a way that will reduce errors and improve efficiency. As will be seen below, various efficiency related parametric data may be measured by suitable performance modules associated with the work environment 208. Further, in one arrangement, an ARM rendering engine associated with ARM module 214 may be constantly improved using the feedback from ML Module 1, e.g., first ML module 222, via a feedback communication interface 221. In an additional, alternative or optional embodiment, ARM 214 may be configured to interact with the workers 204-1 to 204-N, e.g., in a query-response mechanism to improve the AR rendering (i.e., construction of digital representations of actions responsive to the guidance messages) in order to facilitate a more accurate AR rendering process in an iterative manner. For example, ARM 214 may be configured to interact with a worker to offer the ability for the worker to cycle through several representations/renderings until she/he finds one that is more suitable; or even suggest with a suitable movement (e.g., a hand gesture) how best the AR content should be represented in the future. By way of further illustration, ARM 214 may be configured to interact with a worker to offer the ability for the worker to engage in speech recognition interactions (e.g., the worker could ask for missing information from the AR rendering engine with respect to a specific task, such as "show me which valve"). Skilled artisans will recognize that such interactions and worker-specific selections of particular renderings/representations may be fed back via a reverse feedback path 227, along with other feedback signals to the first ML module 222 for training the applicable machine leaning techniques for future tasks. Accordingly, feedback paths 221 and 227 may be operative as a cyclical or complementary feedback loop arrangement operating between ARM 214 and associated ML module 222.

Further, although not shown separately, a query reception module may be associated with ARM 214 and/or RMCM 212 for receiving various types of task-assistance related queries emanating from workers 204-1 to 204-N. In one embodiment, queries may be received at ARM 214, which may be propagated to the experts via RMCM 212. In another embodiment, queries may be received at RMCM 212. As such, example queries may comprise voice, visual, text, data, or other types of input, including AR/MR based input (e.g., pointing/gesturing to a machine or equipment).

As noted previously, a variety of AR devices 206 may be provided for use by workers 204-1 to 204-N for purposes of an embodiment of the present disclosure. Preferably, ARM 214 may be configured to send suitable AR/MR content depending on the type of AR devices used by the workers by way of appropriate interfacing 205. In an additional or alternative arrangement, such AR/MR content could be complemented by other media such as, e.g., written content (text message), audio content (via phone), etc. ARM 214 may therefore be configured in some example embodiments to provide digital representations of various sensory data for AR rendering purposes, e.g., without limitation, visual, auditory, tactile, olfactory, vibrational, and the like. It should be appreciated that rendering for purposes of the patent disclosure relates to the actual AR content and its visualization in terms of colors, shapes, sounds, etc. that may be suitable for each context based on the proper digital representations thereof corresponding to the particular expert guidance or suggestions. As to environmental and contextual data sensing, an ORS/SMaS module (not specifically shown in this FIG.) may be provided similar to the arrangement set forth in FIG. 1 described hereinabove. As previously set forth, such data is representative of various pieces of data collected by the workers in the field around a given task, which could be obtained through or generated by the AR/MR equipment's sensors, direct input from the workers, or via other sensor instruments in place, collectively shown by an environmental data interface 216A relative to the work environment 208. Similarly, a response action interface 216B exemplifies one or more response actions to be taken or performed by a requesting worker responsive to the AR renderings received from ARM 214 via interface 205 with respect to the specific task.

A Task Performance Computation Module (TPCM) 218, which may be co located in association with the work environment 208 in some embodiments, may be configured to measure, obtain, estimate, or otherwise determine the effect of the action(s) taken or performed by the workers. For example, such measurements or determinations may be made based on actual system KPIs or received from workers, and/or remote expert's observed feedback. In similar fashion, a Human Performance Computation Module (HPCM) 220 may be provided in association with the work environment 208 in some embodiments for measuring, estimating, obtaining or otherwise determining the effect of the AR rendering and how the action proposed by the expert (e.g., via RMCM 212) was "translated" or "transformed" for the worker at the associated AR/MR equipment 206. For example, an embodiment of HPCM 220 may be configured to measure the error made by the worker or the accuracy and speed at which the task was performed. In some arrangements, data from TPCM and after-the-fact expert feedback (not specifically shown in FIG. 2), may also used to measure the performance. Skilled artisans will recognize that such information may help further improve AR rendering for a similar context (i.e., any particular combination of tasks, environment, worker and worker equipment) in the future.

In an example implementation, ML module 224 associated with experts 215 may receive or obtain as input all data received by experts (e.g., as part of data input 210) as well as the expert's recommendation/guidance (e.g., through RMCM 212 via interface 223). Further, ML module 224 may also obtain TPCM results via interface 225. ML module 224 may be configured to build a model to replicate the expert's recommendation with the best TPCM results for that specific task/context. As noted before, after proper training, such a model may be used as an expert bot or autonomous cognitive system in some implementations. Additionally or alternatively, such a model may also be used to assist the experts in their decision-making. Moreover, such a trained model may be configured to train the experts in different domains of expertise (e.g., experts could be specifically knowledgeable at certain tasks and the trained model may assist them and teach them to become experts at other tasks). In some arrangements, a model may need to be built per task, which may be initially trained based on and/or responsive to a simulated contextual setting with reference to the specific task before the system goes online (e.g., the training taking place prior to providing any guidance to the workers). An optional arrangement involving the training of ML models based on simulated contextual settings may be referred to as "digital twinning," wherein a digital twin is a simulated version of an actual physical object/equipment and associated process. Example implementations involving a digital twin in association with an AR-rendering platform will be set forth further below.

With respect to the interactions between ML module 222 and ARM 214, the functionality of ML module 222 may be configured to build an ML model for the best rendering in AR of a given expert recommendation for a given context, preferably in a trainable manner. Example performance-based feedback inputs (e.g., HPCM data via interface 219 and information from ARM 214 via interface 227) may be utilized by appropriate ML techniques and systems for generating suitable output to be fed back to ARM 214 via the feedback communication path 221. One skilled in the art will appreciate that such feedback mechanisms, which may be implemented optionally, can replace or improve the typical user testing required in a given contextual scenario for the best rendering of a given task/action. Accordingly, ML module 222 may be configured to learn most optimal rendering options/scenarios for each context (i.e., task, environment setting, worker setting, and the like). By way of a simple illustrative scenario, an example rendering could be to use a tick arrow in particular color (e.g., blue) and voice direction for worker [n1] in environment [e1] or use a flashing arrow in another color (e.g., red) and no voice direction for the same worker [n1] and environment [e2]. It could be that [e2] is a noisy environment (e.g., as sensed by the AR device) and that rendering of expert guidance in audio (i.e., voice direction) would be useless to the worker in such an environment.

According to certain embodiments, an exemplary implementation of the foregoing system architecture 200 can be configured to start with preconfigured values (e.g., initial default settings), which may be improved in an automated fashion by building suitable ML models in ML modules 222 and 224 over a period of time and/or until a certain expected performance convergence is achieved. As previously mentioned, such initialization and preconfiguration with ML module 224 may be effectuated by using the digital twin of a given environment/process. In an analogous fashion, initialization and preconfiguration for ML module 222 may commence with one or more default rendering settings (e.g., using the same rendering for all contexts) and progressively learning to differentiate among the various contexts as the system goes online. As noted elsewhere in the present patent disclosure, "context" may broadly refer to various pieces of information related to the task at hand, the environment and the specific worker in a number of combinations and sub-combinations, along with other pertinent data that may be obtained from third-party sources in some example implementations. Specific examples of at least some of such contextual components will be set forth below in the description of an ML module implementation below (e.g., relative to ML modules 222/224). As a further illustration, it should be appreciated that example task information context may comprise a list of possible actions for a given object within the scope of a task, which may be obtained, generated or otherwise determined from product manuals and other relevant technical publications via online and/or manual data entry.

As previously noted, the industrial environment/processes may be modeled using a digital twin in an optional arrangement according to certain embodiments. For instance, a given digital twin can have various roles in the system presented above. In one example, the expert may first test the recommendation on the digital twin, and based on expected TPCM output, make a decision as to the best recommendation with respect to an assistance query from a worker. In another example, ML module 224 may be pre-trained using digital twin data, and then learn from real world data once the system is online. As a still further example, an optional arrangement may involve a training scenario wherein the digital twin models themselves could be improved using the data from the live system (e.g., from data input module 210, ORS/SMaS data associated with the work environment 208, actions taken by the workers relative to different tasks/queries, as well as TPCM and HPCM outputs, etc.).

Figure 3:
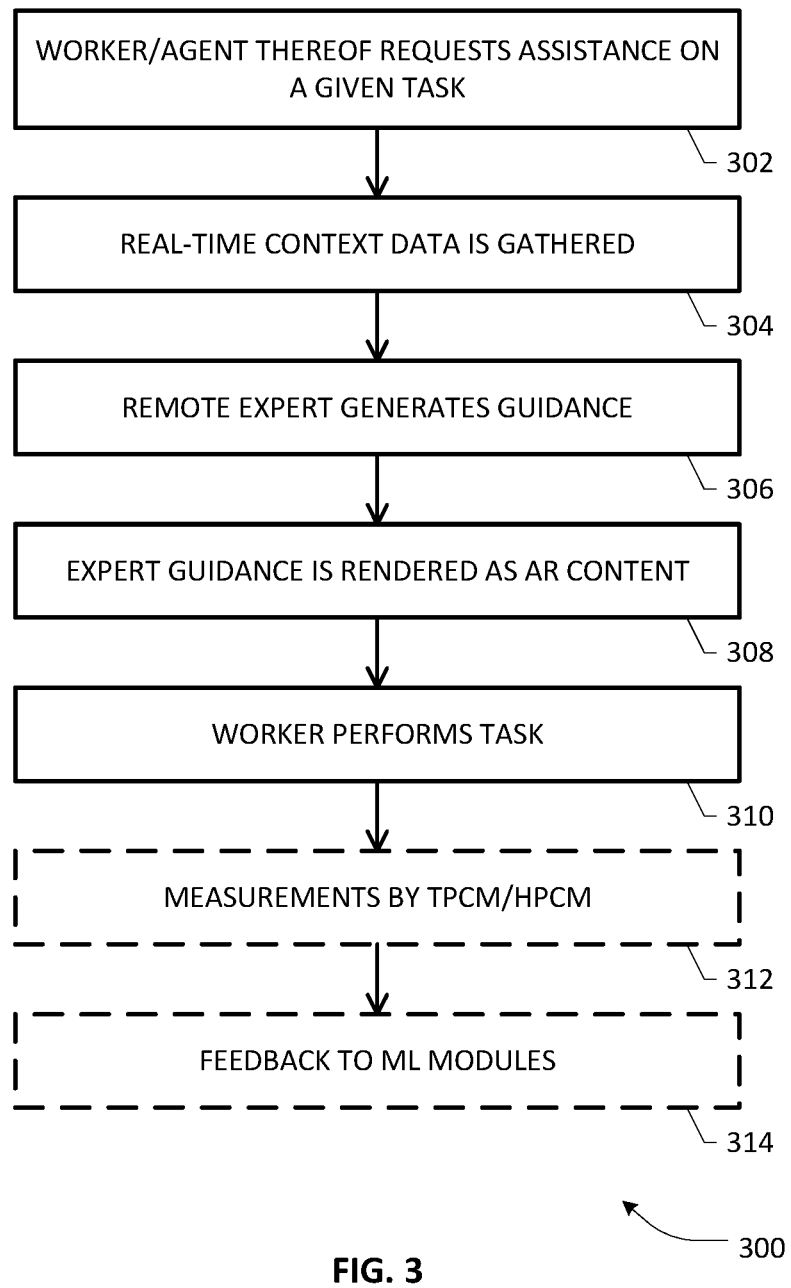
FIG. 3 is a flowchart of various blocks, steps and/or acts that may be (re)combined in one or more arrangements, with or without additional flowcharts of the present disclosure, for effectuating remote assistance according to one or more embodiments of the present patent disclosure.
Figure 5A:
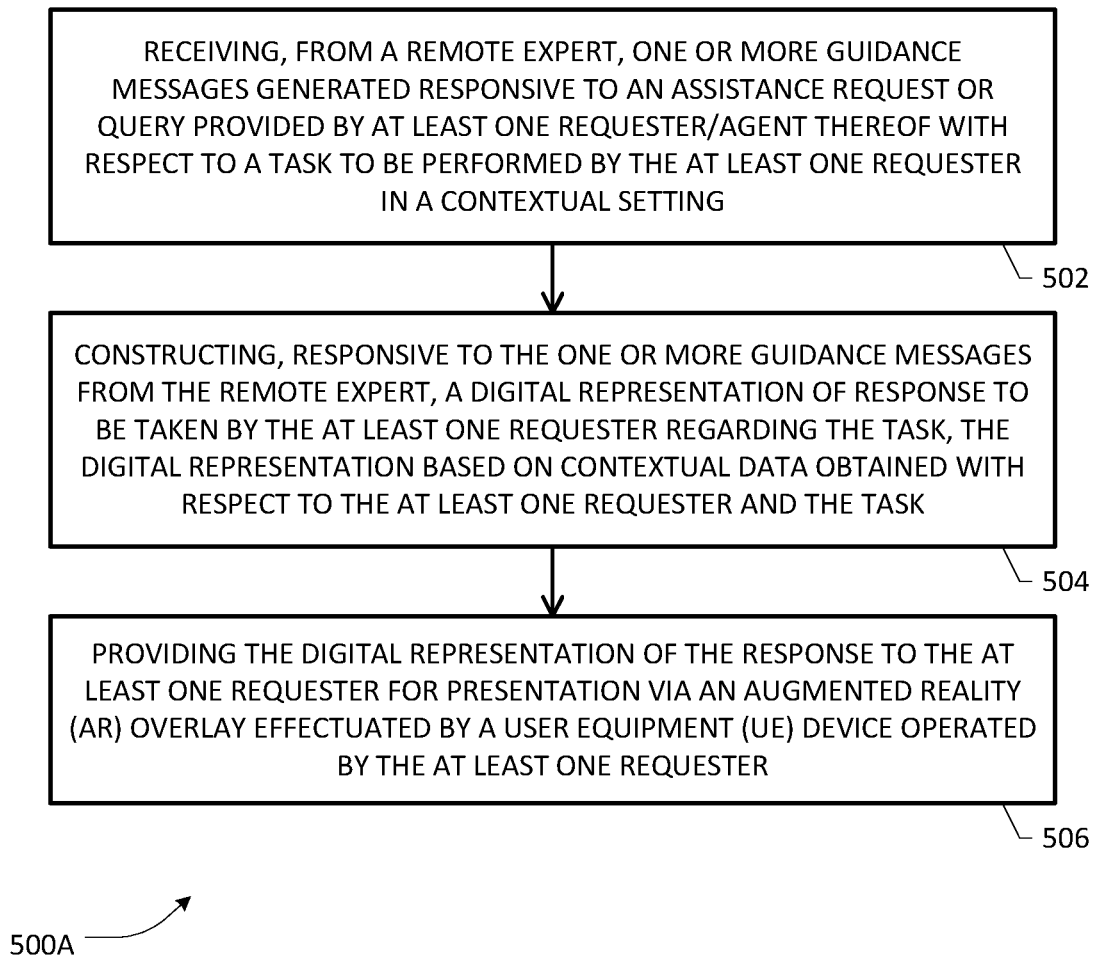

Turning to FIG. 3, depicted therein is a flowchart of an overall process 300 involving various blocks, steps and/or acts that may be (re)combined in one or more arrangements, with or without additional flowcharts of the present disclosure, for effectuating remote assistance according to one or more embodiments of the present patent disclosure. At block 302, a worker requires assistance with respect to a given task and generates one or more suitable queries. As noted elsewhere in the present disclosure, an example worker/requester may be a human and/or associated agent or proxy that generates a request on behalf of and/or in association with the worker. At block 304, real-time context data is gathered. As set forth hereinabove, such data may comprise various pieces of data relating to the work environment, object identification, task data and the worker data, etc. At block 306, a "remote" expert generates appropriate guidance, which may be rendered as AR content for worker consumption by using an ARM (block 308). At block 310, the worker consumes or uses the AR content for performing a response action with respect to the task, which may involve commission or omission of an act. In optional, additional or alternative arrangements, process 300 may also involve obtaining measurements by TPCM/HPCM functionalities associated with the work environment (block 312), which may be fed back to suitable ML modules (block 314) as described previously. The optional nature of blocks 312 and 314 are indicated with the dashed outlines in FIG. 3.

In one implementation, process 300 may be repeatedly performed and/or may be executed in parallel for multiple workers and/or tasks (e.g., in a multithreaded fashion). Although the functionalities of ML modules are not specifically shown in the flowchart of process 300, it should be understood that an implementation of block 306 may involve the generation of expert guidance based on input modulated or enhanced by an ML module or an expert bot using such ML module. Likewise, an implementation of block 308 may also involve constantly/dynamically or periodically improving an AR content generation engine based on suitable ML techniques associated therewith.

In a still further variation, an example process of expert assistance (e.g., process 300) may be triggered by an entity on behalf of and/or in combination with the worker, wherein such entity may comprise a machine or proxy that may be configured to generate requests based on supervision of the worker performing a task. By way of illustration, a camera or other image-capturing device may be configured to oversee the work done by a human worker and a computer/machine vision model may be configured to trigger an alarm or request when a performance specification is not being met, e.g., to request the assistance of a remote expert. Likewise, a human agent may trigger a request or query for assistance on behalf of another user as well. It should be appreciated that such variations are contemplated within at least some of example process embodiments of the present disclosure, e.g., at least as part of block 302.

FIGS. 4A and 4B depict block diagrams of ML modules and associated functionalities that may be used in association with an example ARRA platform according to one or more embodiments of the present patent disclosure. In particular, reference numeral 400A of FIG. 4A refers to a functional block diagram relative to an ML module 404 operative with one or more experts as set forth above, being representative of ML Module 2 or RX-ML module 224 shown in FIG. 2. Broadly, ML module 404 may be configured to execute a suitable self-training process, e.g., responsive to one or more feedback information loops. For instance, ML module 404 may obtain learning from actual experts on various best remote guidance options for any context composed of environment setting(s), task(s), queries and worker(s), wherein a trained ML model can be used to create expert bots and/or to assist human experts with their decision-making according to certain embodiments. A plurality of input sources 402 may be provided with respect to ML module 404, which may comprise a number of components as further exemplified below. In one implementation, a first set of data inputs may comprise KPIs and parameters related to a given asset, shown at block 403A, which may include all or portion(s) of the data collected at data input blocks 210 and ORS/SMaS 216A shown in the system architecture 200 of FIG. 2. By way of illustration, such data could be current readings from a gauge of a pressure regulator valve (i.e., referred to as an "asset") that needs manual adjustment by the worker, which may be provided via open standard file formats that use human-readable text transmit data objects consisting of attribute-value pairs and array data types or any other serializable values. In an example implementation, such a format may comprise a JavaScript Object Notification (JSON) format that may be used for stateless, real-time communications between entities (e.g., server/client). Example JSON format of such input is as shown below. Although in this example "required action" says "reduce", it will be realized that only the expert may know by how much and how to reduce the pressure.

```
{
"assetID": 54832123382418,
"assettype": "valve",
```

-continued

```
"assetcontrols": "pressure",
"metric": "psi",
"gauge reading": 150,
"timestamp": 1519944868,
"abnormal": true,
"requiredaction": "reduce"
}
```

Another set of data components may comprise context and monitored/sensed data, shown at block 403B, which may also be part of the data collected at data input blocks 210 and ORS/SMaS 216A shown in FIG. 2. By way of illustration, context data around a given task may include, without limitation, environmental data, task data, and worker data, as previously noted. In an example work environment, environment data could be asset ambient temperature levels, noise levels as well as video feeds, etc. Task data may include asset data and actual actions that may be possible such as performing a procedure or reporting/troubleshooting an asset.

For example, environment data relating to a valve asset may be described in JSON format as below:

```
{
"assetID": 54832123382418,
"timestamp": 1519944868,
"am bienttemperaturecelsius": 25,
"am bientnoisedB": 70
}
```

In analogous fashion, video feed data may comprise frame-by-frame of pixel information from any number of video sources of the work environment using a variety of formats, e.g., PNG format, in an example implementation.

With respect to task data, for example, data for a valve-related task may be described as possible actions on a specific asset related to the task (as mentioned above this information may be obtained from experts or product manuals). In an example JSON implementation such data may be formatted as below:

```
{
"assetID": 54832123382418,
"actiontype": "turnvalve",
"actionvaluemetric": "degrees",
"actiondirection reduce": "counterclockwise",
"actionreducemaxvaluestep": 180,
"actiondirectionincrease": "clockwise",
"actionincreasemaxvaluestep": 90
}
```

Worker data may comprise specific information about the worker on the task, such as e.g., left/right-handed worker, ambidextrous capabilities, differently-ab led mental/physical faculties, color-sensitive eyesight, visual/auditory acuity, training/education skills, language skills, etc., as well as a list of tools currently carried by and/or available to the worker or a list of tools the worker has been trained to work with. A simplified example of worker data in JSON format is shown below:

```
{
"workedID": 201746382913,
"workername": "John Doe",
```

```
"workerheightcm": 179,
"leftrighthanded": "right",
"toolsetscarried": {
   "adjusting screw 20 mm": true,
   "adjusting screw 40 mm ": false,
   "adjusting screw 60 mm ": true
},
"workerfamiliaritywithassetmin0max5": {
   "assetID": [54832123382418, 54832123382419,
      54832123382420],
   "level": [4,5,0]
}
}
```

In some example implementations, there may be other data components (shown at block 403C), which may relate to other manually entered data that is not typically automatically sensed as part of the data collected at data input blocks 210 and ORS/SMaS 216A shown in FIG. 2. An example JSON object of such data relating to the illustrative value asset scenario may be formatted as below:

```
{
   "assetIDvisualinspection": [
      ["54832123382418", "broken"],
      ["54832123382419", "rusted"],
      ["54832123382420", "good"]
   ]
}
```

In some example implementations, a plurality of outputs 406 may be generated, which may comprise expert's suggestion(s) 407A, including the actual output provided via or from RMCM 212 to ARM 214 shown in FIG. 2. For example, in the above valve-task scenario, such guidance could be to turn the valve knob 90 degrees to the right (counterclockwise). The action data for turning the knob on the valve may be described as follows:

```
{
   "assetID": 54832123382418,
   "actionID": 2017128272,
   "actiontype": "turnvalve",
   "actiondirection": "counterclockwise",
   "actionvaluemetric": "degrees",
   "actionvalue": 90
}
```

Another set of outputs 407B may comprise expected TPCM measurements with respect to the task being completed. Also, in some implementations, actual TPCM values may be measured afterwards wherein the actual TPCM output is obtained after the worker performs an action according to the expert guidance, which may be propagated to the ML module 404. In some implementations, comparisons between the actual and expected TPCM values may also be provided as feedback to the ML module 404. Accordingly, a feedback loop path 410 involving suitable elements such as comparators, error signal generators, collectively shown as element 408, may be provided as part of the functional block diagram 400A relative to the ML module 404.

By way of illustration, a "completionscore" may be provided in an example valve-task scenario where a score on a scale of maximum value of 100 is operative to determine or indicate how well the desired performance was achieved. A corresponding TPCM data object in JSON format is illustrated below:

```
{
   "assetID": 54832123382418,
   "actionID": 2017128272,
   "metric": "psi",
   "gauge reading before": 150,
   "gauge reading after": 75,
   "completionscore": 100
}
```

Skilled artisans will recognize that although ML module 404 is shown in FIG. 4A as a single block, the machine learning functionality may be implemented using one or more ML techniques, processes or algorithms and models (e.g., neural networks) as well as rule-based systems. In general, a variety of techniques such as, e.g., "big data" analytics, artificial intelligence, convolutional neural networks (CNNs), fuzzy logic learning, pattern recognition, support vector machines (SVMs), support vector networks (SVNs) and related techniques may be employed in a suitable combination or sub-combination with respect to effectuating a learning process as part of ML module 404. In some example embodiments, real-time object recognition and tracking in 3D space over time may require a separate CNN with respect to the context data processing. On the other hand, for the association of context to an action recommendation, a rule-based system may be used if the action space is small. Accordingly, it should be appreciated that different ML models may be used, standalone or in concert, e.g., depending on the dataset dimensionality, to achieve the requisite overall ML functionality with respect to generating a converged mapping/transformation between an input feature set/space $\{x_2\}$ and an output results set/space $\{F_2(x_2)\}$ at least according to some example implementations of the system architecture 200 of FIG. 2.

Directing attention to FIG. 4B, an apparatus 400B depicted therein is representative of a functional block diagram relative to an ML module 454 that may be configured to operate as ML Module 1 or AR-ML module 222 of the system architecture 200 shown in FIG. 2. Preferably, according to certain embodiments, ML module 454 may be configured for learning from past AR rendering history of the system architecture 200 as well as associated HPCM outputs in order to be able to suggest best or most optimal AR renderings for a given context. Similar to the ML module 404 above, a plurality of input sources 452 may be provided with respect to ML module 454, which may comprise a number of components as further exemplified below. For example, a first set of data inputs 453A may comprise context and monitored/sensed data, similar to the context data input 403B with respect to ML module 404 of FIG. 4A. Accordingly, such data input is generally obtained as part of the data collected at data input blocks 210 and ORS/SMaS 216A shown in FIG. 2. Although a similar description of the context data 453A may be applicable here, more emphasis, significance or weight may be accorded to the environment data and worker data with respect to an example implementation of ML module 454. By way of illustration, context data may also include the current location of the worker's AR equipment (e.g., for rendering purposes). Another set of data inputs 453B may comprise the expert's suggestions, recommendation or guidance (e.g., comprising an omission or commission of a specific action relative to the task at hand). Analogous to the expert's suggestion(s) 407A set forth in FIG. 4A, expert guidance input 453B here may also comprise the actual output provided via or from block 212 to ARM 214 in FIG. 2.

Accordingly, a similar description of such data may be applied here as well, mutatis mutandis.

In some example implementations, a plurality of outputs 456 may be generated by ML module 454 relative to AR rendering as well as related performance measurements, including human/worker performance metrics. For instance, a rendering output component 457A may comprise the rendering of action(s) suggested by the expert which is the AR rendering (i.e., construction of suitable digital representations of the expert's recommendation based on the context (task, environment, worker, etc.) including the AR gear carried by the worker. By way of illustration, the suggested action data from the example scenario above is repeated below as an action data object [a1]. For simplicity, an example position vector may be defined as "absolutepositionscm" vector that only shows three points for the start, middle and head of a curved arrow in centimeters relative to an object. However, in a more practical implementation, additional points may also be described in this field for AR rendering along with the material and other parameters of AR objects. An example JSON action data object [a1] repeated from the valve-task scenario above is as follows:

```
{
"assetID": 54832123382418,
"actionID": 2017128272,
"actiontype": "turnvalve",
"actiondirection": "counterclockwise",
"actionvaluemetric": "degrees",
"actionvalue": 90
}
```

With respect to rendering of action data object [a1], the following is an example output data object in JSON format:

```
{
"ARdeviceID": 20173228476349,
"actionID": 2017128272,
"renderingID": 20171282723484718,
"ARdeviceType": "GoogleGlassEE",
"objectID": "curvedarrowleft",
"absolutepositionscm": {
  "x": [10, 5,0],
  "y": [0, 0, 0],
  "z": [0, 0, 0]
},
"opacity": 0.63,
"color": {
  "R": 0,
  "G": 0,
  "B": 255
}
}
```

Another set of outputs 457B may comprise expected/measured HPCM values relative to the performance of the action recommended by the expert as rendered in AR, including a suitable scoring/grading mechanism to indicate how good the AR rendering was after the worker has performed the task at hand. In some implementations, the actual HPCM values may be fed back to ML module 454. Accordingly, a feedback loop path 460 involving suitable elements such as comparators, error signal generators, collectively shown as element 458, may be provided as part of the functional block diagram 400B relative to the ML module 454. Example values could be a precision score or some objective parameter calculated from the TPCM module 218 (which would represent how well the task was accomplished) and/or a subjective score given by the remote expert and the worker, as well as additional parameters such as task completion time, etc. Similar to the TPCM's "completionscore" parameter, a suitable parameter such as "taskcompletionscore" may be configured with respect to an HPCM module in an example scenario, where a score of a maximum value of 100 represents best AR rendering. A corresponding HPCM data object in JSON format is illustrated below:

```
{
"ARdeviceID": 20173228476349,
"actionID": 2017128272,
"renderingID": 20171282723484718,
"ARdeviceType": "GoogleGlassEE",
"objectID": "turnknobarrowleft",
"taskcompletionscore": 80
}
```

For example, subjective feedback from the worker may be provided in form of rank ordering data such as, e.g., (i) a 5-star rating of the worker's experience; (ii) feedback survey, and the like. As one skilled in the art will recognize, various cardinal, ordinal, quantitative and/or qualitative metrics may be employed in scoring such task completion and/or performance metrics depending on a particular implementation.

Similar to the implementation of ML module 404 is shown in FIG. 4A, skilled artisans will recognize that although ML module 454 is shown in FIG. 4B as a single block, the machine learning functionality may be implemented as one or more ML techniques, processes or algorithms and CNN models as well as rule-based expert systems. Specific to AR rendering, a set of best rendering options in AR may be selected from a list of candidate rendering objects, e.g., including but not limited to visual, auditory, tactile, etc., depending on the context and the AR equipment associated with the worker. Determination as to the actual rendering objects to use and the parameters with which they need to be configured may be learned by ML module 454 for continuous improvement of the AR rendering engine associated therewith. Accordingly, it should be appreciated that a variety of ML models and/or rendering engines may be used, standalone or in concert, to achieve the requisite overall ML functionality with respect to generating a suitable rendering based on input feature set/space $\{x_1\}$ that is mapped to and/or transformed to an output results set/space $\{F_1(x_1)\}$ comprising the rendering output at least according to some example implementations of the system architecture 200 of FIG. 2.

FIGS. 5A-5E depict flowcharts or flowchart portions of various blocks, steps and/or acts that may be (re)combined in one or more arrangements, with or without additional flowcharts of the present disclosure, for effectuating further aspects of an AR-based remote assistance platform according to one or more embodiments of the present patent disclosure. An example process 500A executing at a node, network element, etc., preferably configured as an ARM node, may commence with receiving, from a remote expert, one or more guidance messages generated responsive to an assistance request provided by at least one requester with respect to a task to be performed by the at least one requester in a contextual setting (block 502). Responsive to the one or more guidance messages from the remote expert, a digital representation of a response may be constructed, wherein the response may comprise action or lack/withholding of action to be effectuated by the at least one requester regarding the task. Preferably, construction of the digital representation may be based on contextual/environmental data obtained with respect to the at least one requester as well as the task (block 504). The contextualized digital representation of the response action may be transmitted or otherwise provided to the at least one requester for presentation via an AR overlay effectuated by an AR/MR UE device operated by the at least one requester (block 506). In some embodiments, the construction of the digital representation is facilitated based at least in part upon rendering output received from a first machine learning (ML) module (e.g., AR-ML module 222 shown in FIG. 2) configured to automatically generate AR rendering of remote expert guidance messages in a trainable manner.

Depending on implementation, a further set of variations, modifications, etc., may be effectuated in conjunction with the example process 500A, preferably resulting in a number of combinations that may be realized in accordance with the teachings herein. For example, as depicted in block 512 of FIG. 5B, an embodiment may include a further process 500B of training the first ML module 222 responsive to feedback received from a performance measurement entity (e.g., such as an HPCM set forth hereinabove), which may be local, remote, network-centric or cloud-based, etc. with respect to a work environment, configured to measure, obtain or otherwise determine one or more performance/rendition metrics, e.g., (i) accuracy of the construction of the digital representation of the action; (ii) indication of performance quality in executing the action by the at least one requester with respect to the task, etc. In one embodiment including a further process 500C, generation of one or more guidance messages may be facilitated based at least in part upon feedback received from a second machine leaning (ML) module (e.g., RX-ML module 224 shown in FIG. 2) configured to provide feedback to the remote expert(s) with respect to task performance and completion data provided by a task performance computation module (TPCM), which may be disposed at different architectural levels, e.g., local, remote, network-centric or cloud-based, etc. with respect to the work environment, as set forth at block 514 of FIG. 5C. In one embodiment, process 500A may be augmented to include a further process 500D of interacting with the at least one requester via a query-response mechanism to improve the digital representation of the response action for facilitating a more accurate AR rendering, as set forth at block 516 of FIG. 5D. In one embodiment, process 500A may be augmented to include a further process 500E by training at least one of the first ML module and the second ML module using a simulated contextual setting with respect to the task, the training taking place prior to providing any guidance messages to the at least one requester, as set forth at block 518 of FIG. 5E.

Figure 6A:
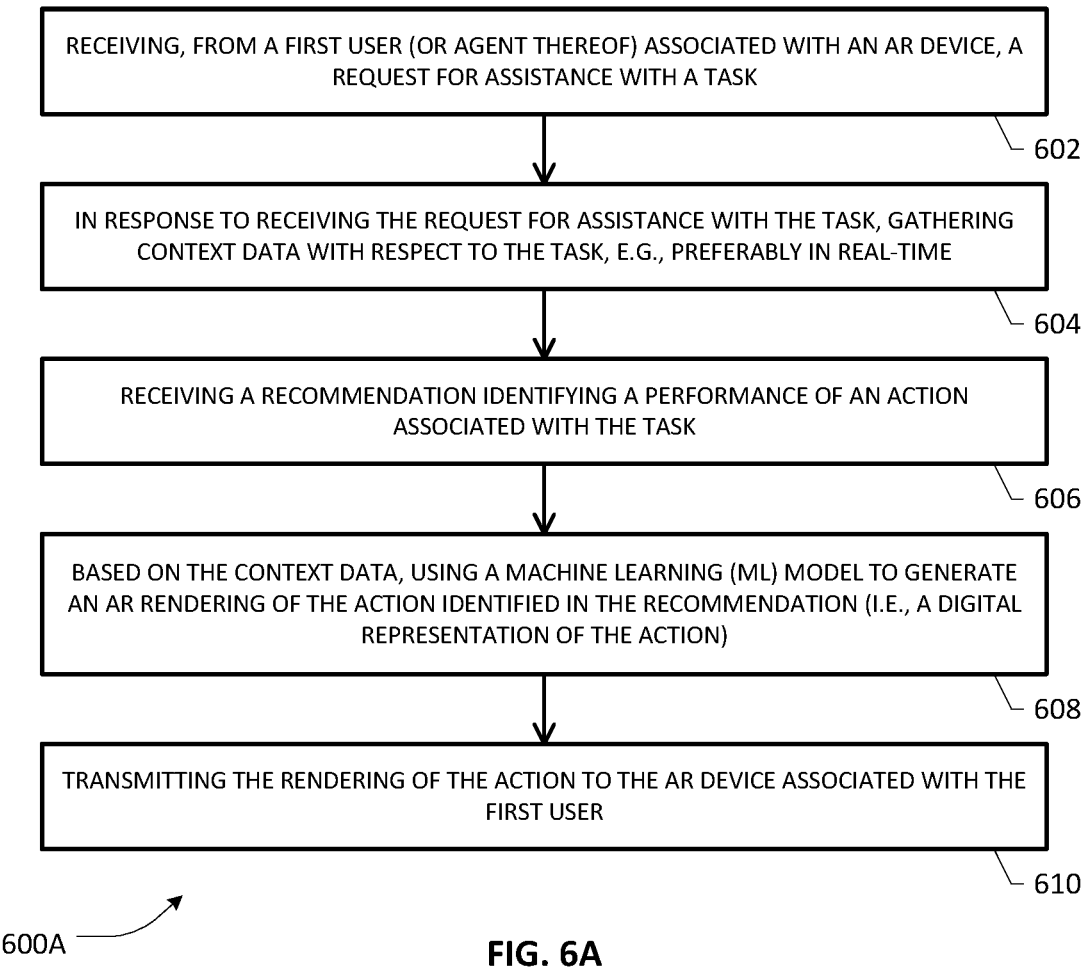
FIGS. 6A and 6B depict flowcharts of various blocks, steps and/or acts that may be (re)combined in one or more arrangements, with or without additional flowcharts of the present disclosure, for effectuating still further aspects of a remote assistance platform according to one or more embodiments of the present patent disclosure.
Figure 6B:
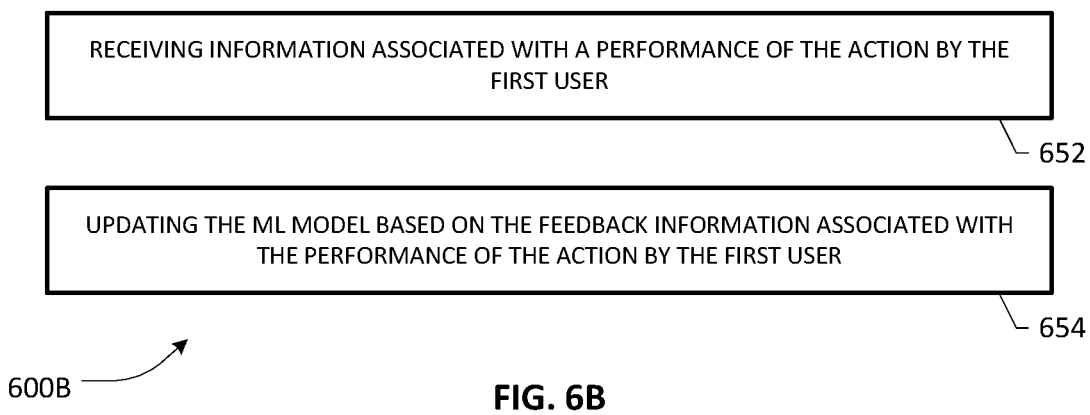

FIGS. 6A and 6B depict flowcharts of various blocks, steps and/or acts that may be (re)combined in one or more arrangements, with or without additional flowcharts of the present disclosure, for effectuating still further aspects of an AR-based remote assistance platform according to one or more embodiments of the present patent disclosure. An example process 600A set forth in FIG. 6A may commence with receiving a request for assistance with a task (block 602), e.g., from a first user associated with an AR device and/or an agent/proxy on behalf thereof. In response to receiving the request for assistance with the task, process 600A involves gathering context data with respect to the task, e.g., preferably in real-time (block 604). In one embodiment, the context data may include information associated with a previous performance of a response action by the first user or one or more other users. In other particular embodiments, the context data may be a current location of the AR device and/or sensed data received from the AR device. In still another particular embodiment, the context data may include monitored data associated with an environment in which the task is to be performed. In yet another embodiment, the context data may include user input and/or one or more measurements of performance of a previous action by the first user or a second user. A recommendation identifying a performance of an action associated with the task is received at block 606. In one embodiment, the recommendation may be received from a second user who is an expert. In another embodiment, the recommendation may be received from a computing device configured to automatically generate the recommendation based on the request and the context data.

In a particular embodiment, a centralized node may receive data associated with the task, the user, and/or an environment in which the task is to be performed. The centralized node may then provide that data to the second user and/or generate an expert suggestion that is transmitted to the second user for use in generating the recommendation identifying the performance of the action. In a particular embodiment, the data may be associated with a key performance indicator. In a particular embodiment, the data may be collected from an asset located at a site where the task is to be performed by the first user. In yet another particular embodiment, the data may include video data. In still another particular embodiment, the data may be automatically sensed by the AR device associated with the user.

Based on the context data, an ML-based model is used to generate an AR rendering of the action identified in the recommendation (i.e., a digital representation of the action), as set forth at block 608. Thereafter, the rendering of the action may be transmitted to the AR device associated with the first user (block 610).

Additional variations or enhancements may involve steps or acts set forth in process 600B of FIG. 6B. At block 652, feedback information associated with a performance of the action by the first user may be received. In a particular embodiment, for example, the information may include one or more measurements associated with the performance of the action by the first user. In a particular embodiment, the one or more measurements of the performance of the action may be received from the expert, the first user, or some other entity (e.g., a certification agency). For example, the one or more measurements may include a precision score. In a particular embodiment, an expected level of performance of the action may be generated and the information associated with the performance of the action by the first user may be compared to the expected level of performance of the action. According to certain embodiments, the ML model for the rendering of the action (e.g., AR-ML module 222 shown in FIG. 2) may be revised based on the comparison. Responsive thereto, the ML model 222 may be updated based on the various pieces of the feedback information associated with the performance of the action by the first user (block 654). Other enhancements may involve an RX-ML module, either separately or together with an AR-ML module, for purposes of the present patent disclosure.

Figure 7A:
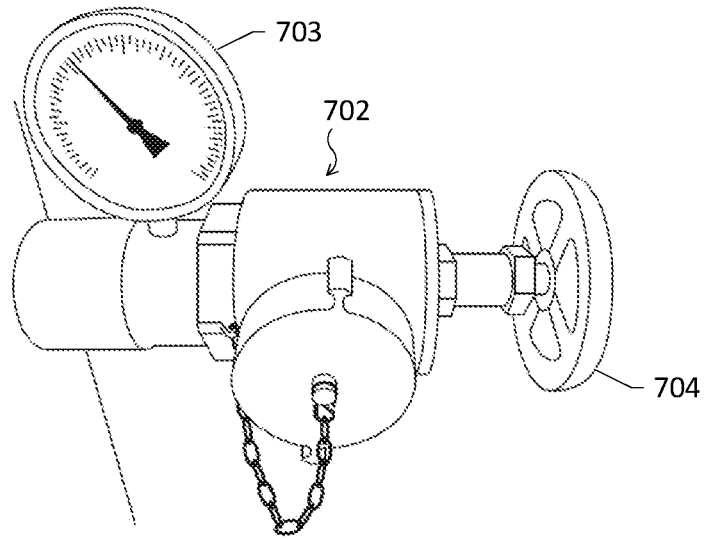
FIGS. 7A-7C depict example AR-based assistance rendering scenarios according to some embodiments of the present patent disclosure.
Figure 7B:
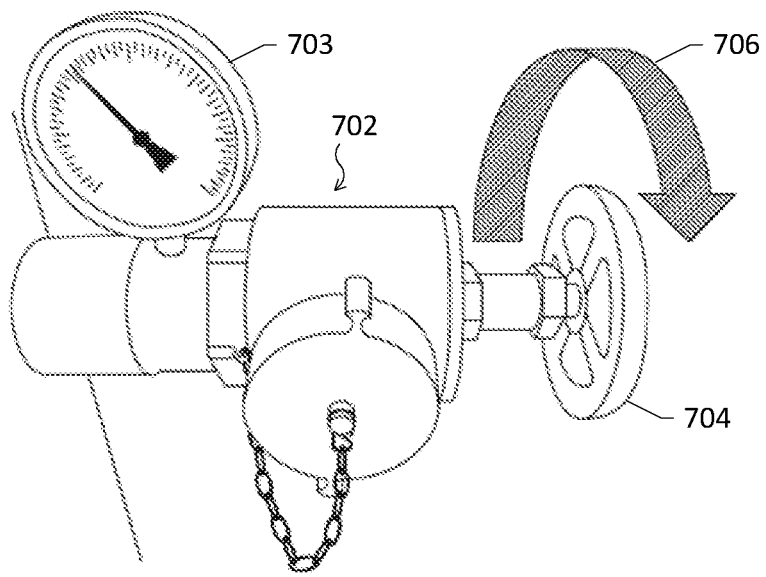
Figure 7C:
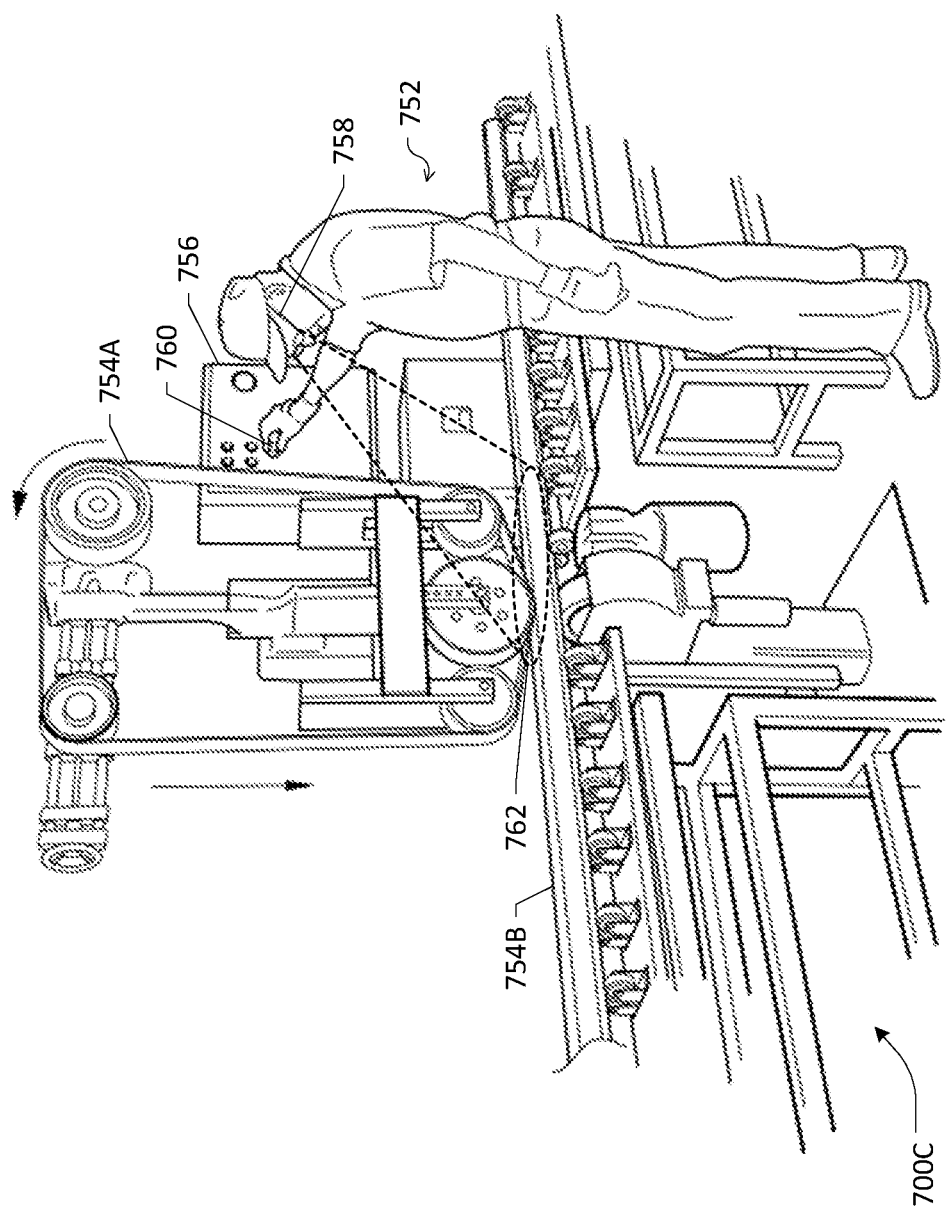

FIGS. 7A-7C depict example AR-based assistance rendering scenarios according to some embodiments of the present patent disclosure. In particular, FIGS. 7A and 7B illustrate views associated with an example valve task, e.g., relative to the valve task example scenario set forth above in reference to the ML module implementations in FIGS. 4A and 4B. Example scenario 700A in FIG. 7A is representative of a worker's FOV without an AR-based assistance rendering, wherein a valve 702, pressure gauge 703 and associated control knob 704 are highlighted. Example scenario 700B in FIG. 7B is representative of the worker's FOV that includes an AR-based assistance rendering, which in this particular illustration is highlighted as a pictograph or pictorial/visual indication 706 (having a particular color and shape, for instance) showing in which direction to turn the control knob 704 of the valve 702.

FIG. 7C depicts a more involved scenario 700C of a factory or workshop environment wherein a rail polishing machine 754A is operated by a worker 752 equipped with an AR/MR device 758 for polishing/milling a rail 754B to a thickness. Responsive to generating suitable queries, e.g., with respect to thickness or other polishing/milling characteristics, material properties, etc., appropriate AR-based rendering may be presented to the worker 752 in an FOV 762 involving AR/MR overlay of rendered assistance and real world objects (e.g., at least a portion of the rail 754B being worked on). Responsive to the received AR-based renderings (e.g., visual and/or auditory), the worker 752 may take an action such as adjusting a control knob 760 of a control panel 756 of the rail polishing machine 754A.

Figure 8:
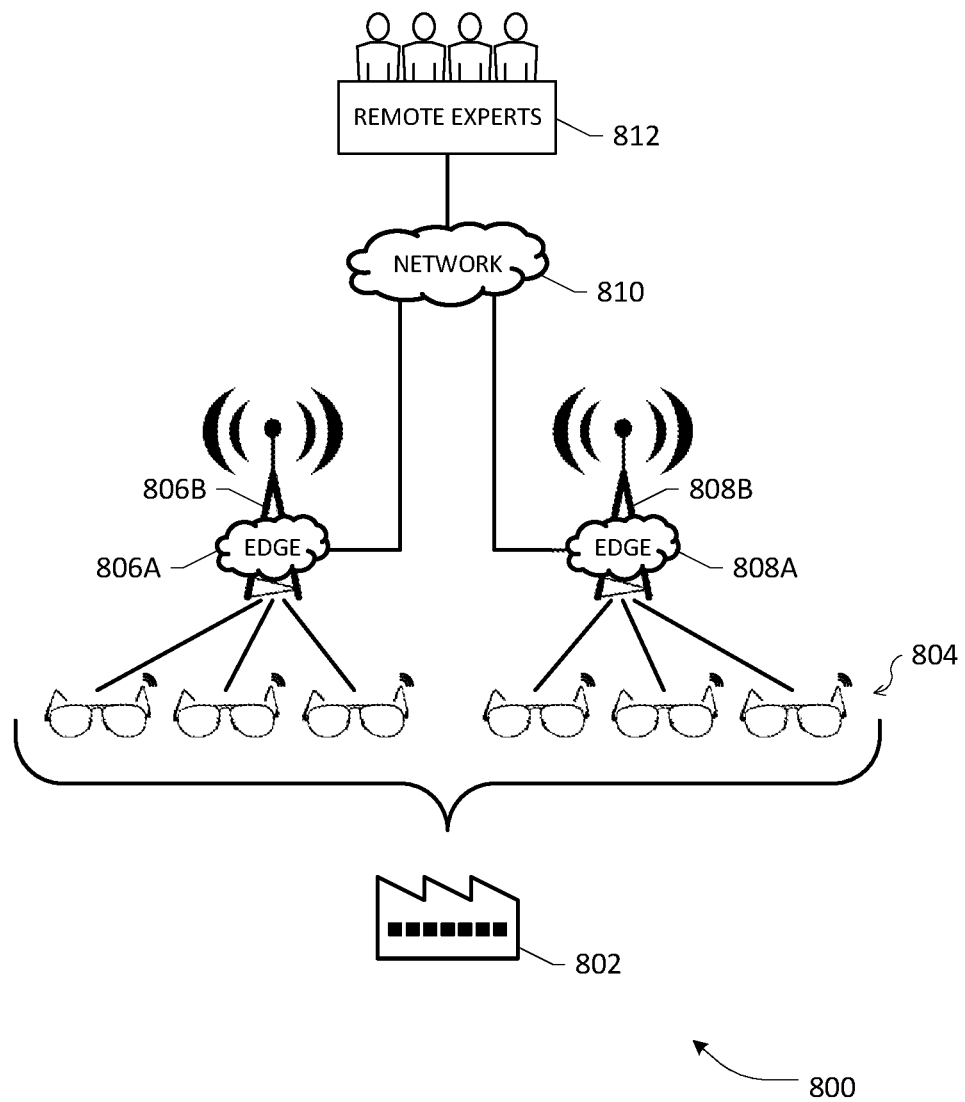
FIG. 8 depicts a cloud-centric implementation of an ARRA architecture according to some embodiments of the present patent disclosure.

As one skilled in the art will clearly recognize upon having reference to the present disclosure, embodiments set forth herein may be implemented in a number of architectural configurations and network hierarchical organizations (e.g., federated networks, non-federated networks, public/private networks, managed/unmanaged networks, etc.), which in some instances may involve distributed/scalable architectures wherein multiple instances of the AR system architecture 200 and/or its constituent modules as shown in FIG. 2 may be deployed. By way of illustration, FIG. 8 depicts a cloud-centric implementation or system 800 of an example AR system architecture according to some embodiments of the present patent disclosure. Example system implementation 800 may include components such as one or more centralized computing nodes associated with a core network 810 and one or more edge computing nodes 806A/808A associated with respective edge/access network infrastructures 806B/808B, which may be implemented using a variety of cellular communications technologies and protocols (e.g., 5G) for connectivity. According to certain embodiments, modules such as ARM 214, TPCM 218, HPCM 220, as well as ML modules 222 and 224 may be hosted in edge compute nodes, or be centralized, or both. For example, according to certain embodiments, ML module 224 may be trained and maintained in the centralized network or cloud 810 while ML module 222 may be distributed per device type, task group, worker group, etc. (i.e., context). Workers 804 of a work environment 802 may be grouped and serviced by different edge networks/nodes 806A/806B and 808A/808B, wherein a common pool of remote experts 812 may be operative to provide AR-based remote assistance via the centralized network 810. In one implementation, a central version of the ML module 224 may be configured to run in a centralized compute node for off-line optimizations and adjustments and optionally with developer input for improvement.

According to certain embodiments, the digital twin processes' simulator engine(s) may be developed/maintained centrally, which may be updated at the edge and periodically synchronized to the central node, preferably based on feedbacks from actual field/work environment. For instance, feedback from field/work environment may be configured to report on an actual context+action by worker→output process sequence, which may be compared via suitable feedback loops for improving the simulator engine(s) associated with the digital twin entities.

Further, in certain embodiments, the AR devices may have reliable and high-speed connectivity (e.g., with a 5G-based interface towards the ARM module 214 shown in FIG. 2) for real-time feedback of video and other sensed data. Depending on the criticality of the task, the various AR devices of an example work environment may use different network slices with varied network quality of service (QoS) in an end-to-end sliced network architecture. In case of network congestion, higher risk/priority tasks may be assigned to or accorded more network resources to minimize business loss. Policy determinations as to what tasks/contexts are higher risk/priority and would cause higher business loss may be co-located in the network/cloud orchestrator's policy management node(s).

Also, the network/cloud resource management associated with an AR-based remote assistance platform may be optimized based on calculated quality of experience (QoE) from the ARM feeds received by each AR device. Techniques such as content-aware modeling, cloud mobile rendering and streaming, etc., may be used to adapt the AR content feed (from ARM 214 to AR devices 206) as well as the sensor data feed (from AR devices 206 to data input block 210 in FIG. 2) depending on available network resources.

Figure 9:
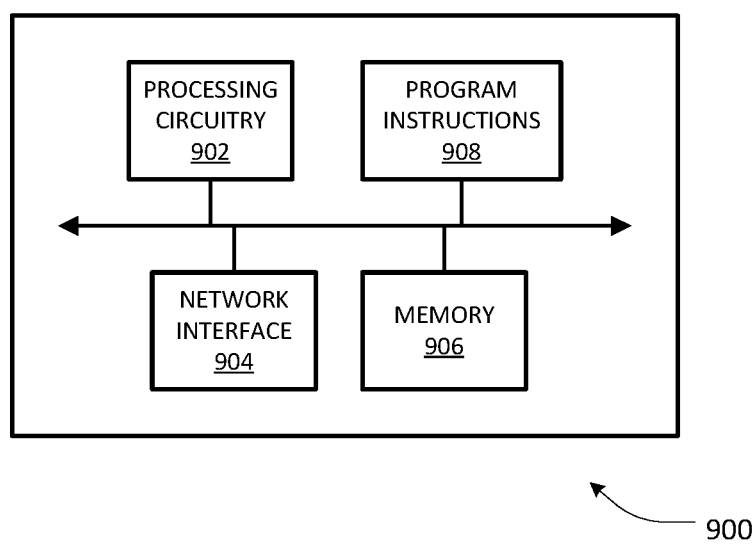
FIG. 9 depicts a block diagram of an apparatus that may be configured as a centralized or cloud-centric node to perform at least some aspects of an ARRA platform for purposes of an example embodiment of the present patent disclosure.

FIG. 9 depicts a block diagram of an apparatus, node, network element, or server that may be configured as a centralized or cloud-centric computing node 900 to perform/implement at least some aspects of an ARRA platform for purposes of an example embodiment of the present patent disclosure. As depicted, the centralized computing node 900 includes processing circuitry 902 (e.g., which may include one or more processors), one or more network interfaces 904, memory 906 and one or more stored program instruction blocks 908. In some embodiments, processing circuitry 902 executes the stored program instructions to provide some or all of the functionality described above as being provided by the centralized computing node 900. Memory 906 may also include further instructions and/or data, which may be executed by processing circuitry 902. Network interface(s) 904 communicate signals to any suitable node, such as a gateway, switch, router, Internet, Public Switched Telephone Network (PSTN), edge network nodes, radio network controllers, or core network nodes, etc.

Processing circuitry 902 may include any suitable combination of hardware and software implemented in one or more modules to execute instructions and manipulate data to perform some or all of the described functions relative to implementing an AR-based remote assistance platform as set forth hereinabove. In some embodiments, memory 906 is generally operable, e.g., in association with modules 908, to store instructions, such as a computer program, software, an application including one or more of logic, rules, algorithms, code, tables, etc. and/or other instructions capable of being executed by a processor. Examples of memory 906 include various types of memory as set forth elsewhere in the present patent disclosure. In some embodiments, network interface 904 is communicatively coupled to processing circuitry 902 and may refer to any suitable device operable to receive input for the centralized computing node, send output from the centralized computing node, perform suitable processing of the input or output or both, communicate to other devices, or any combination of the preceding. Network interface 904 may include appropriate hardware (e.g., port, modem, network interface card, etc.) and software, including protocol conversion and data processing capabilities, to communicate through a network. Other embodiments of the centralized computing node 900 may include additional components beyond those shown in FIG. 9 that may be responsible for providing certain aspects of the network node's functionality, including any of the functionality described above and/or any additional functionality (including any functionality necessary to support one or more embodiments described above).

Figure 10A:
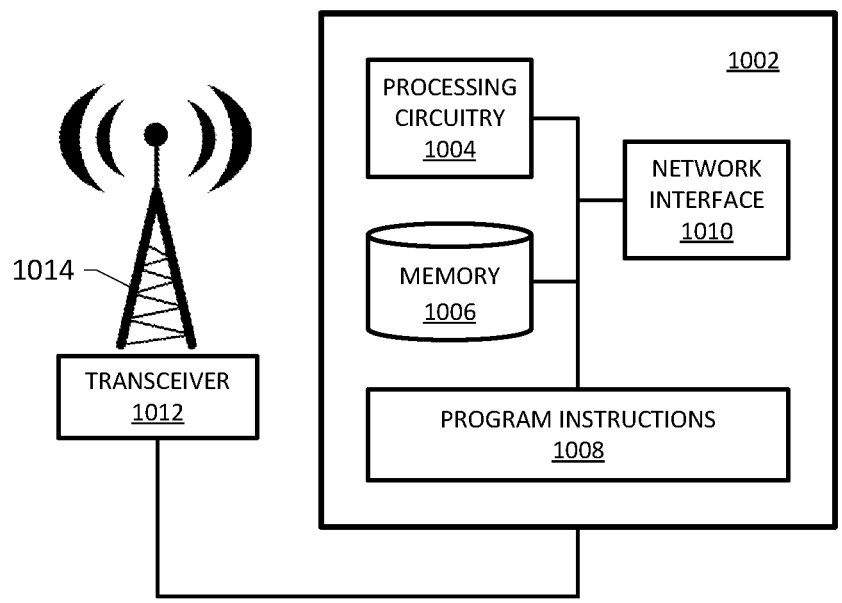
FIGS. 10A and 10B depict block diagrams of an edge node and a wireless device, respectively, that may be configured to perform at least some aspects of an ARRA platform for purposes of an example embodiment of the present patent disclosure.

FIG. 10A depicts a block diagram of an edge node 1000A that may be configured to perform at least some aspects of an ARRA platform for purposes of an example embodiment of the present patent disclosure. Edge node 1000A may be any type of radio network node or any network node that communicates with a UE and/or with another network node. Examples of network edge node 1000A may include, without limitation, a gNB, eNodeB, a node B, a base station, a wireless access point (e.g., a Wi-Fi access point), a low power node, a base transceiver station (BTS), base station (BS), relay, donor node controlling relay, transmission points, transmission nodes, remote RF unit (RRU), remote radio head (RRH), multi-standard radio (MSR) radio node such as MSR BS, nodes in distributed antenna system (DAS), Self-Organizing Network (SON) node, positioning node (e.g., E-SMLC or Evolved Serving Mobile Location Center), MDT, or any other suitable network node. Example edge nodes 1000A may be deployed throughout a network (e.g., in a front-haul network) as a homogenous deployment, heterogeneous deployment, or mixed deployment. A homogeneous deployment may generally describe a deployment comprising the same (or similar) type of edge nodes 1000A and/or similar coverage and cell sizes and inter-site distances. A heterogeneous deployment may generally describe deployments using a variety of types of edge nodes 1000A having different cell sizes, transmit powers, capacities, and inter-site distances. For example, a heterogeneous deployment may include a plurality of low-power nodes, e.g., microcells, small cells, femtocells, picocells, etc., placed within and/or across a macro-cell layout. Mixed deployments may include a mix of homogenous portions and heterogeneous portions.

Example edge node 1000A may include one or more transceivers 1012 coupled to a computing platform or module 1002, which typically comprises processing circuitry 1004 (e.g., which may include one or more processors), memory 1006, and network interface 1010. In some embodiments, a separate stored program instructions block 1008 may also be provided. In general, transceiver 1012 is operative to facilitate transmission of wireless signals to and receipt of wireless signals involving a wireless device (described below), typically via a radio antenna or tower 1014. Processing circuitry 1004 executes instructions to provide at least part of the AR-based remote assistance platform functionality described above. Similar to a centralized network node, the various elements of edge node 1000A including memory 1030, processing circuitry 1004, stored program instructions or code portions 1008 may interoperate to carry out the instructions and communicate appropriate signals to other elements within the edge network, higher-level networks or to the UE devices.

Other embodiments of edge node 1000A may include additional components beyond those shown in FIG. 10A that may be responsible for providing certain aspects of the radio network node's functionality, including any of the functionality described above and/or any additional functionality (including any functionality necessary to support one or more embodiments described above). The various different types of network nodes may include components having the same physical hardware but configured (e.g., via programming) to support different radio access technologies, or may represent partly or entirely different physical components.

Figure 10B:
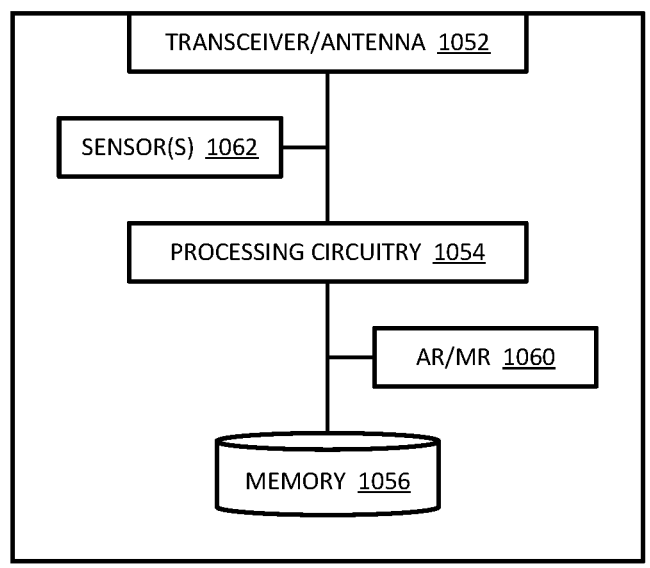

According to certain embodiments, AR/MR devices may communicate with wireless UE devices and/or may be integrated therewith to transmit data to and receive data from edge nodes and/or centralized nodes. FIG. 10B depicts a block diagram of an exemplary wireless AR-capable UE device 1000B according to certain embodiments. UE device 1000B may refer to any type of wireless device communicating with a node and/or with another wireless device in a cellular or mobile communication system and may be associated with appropriate AR/MR gear for effectuating AR/MR display. Examples of UE device 1000B may include a mobile phone, a smart phone, a Personal Digital Assistant (PDA), a portable computer (e.g., laptop, tablet, phablet), a sensor, a modem, a machine-type-communication (MTC) device and/or machine-to-machine (M2M) device, laptop embedded equipment (LEE), laptop mounted equipment (LME), USB dongles, a device-to-device (D2D) capable device, or another device that can provide wireless communication and AR capability. UE device 1000B may also be referred to as a mobile station (STA), an endpoint device, or a terminal in some embodiments. Broadly, UE device 1000B includes a transceiver and antenna arrangement 1052 (e.g., a multi-mode RAN capable multiple-input and multiple-output (MIMO) arrangement), processing circuitry 1054 and memory/instructions 1056. In some embodiments, transceiver 1052 facilitates transmitting wireless signals to and receiving wireless signals from a network node (e.g., edge node 1000A shown in FIG. 10A), typically using an internal or external antenna 1058. Processing circuitry 1054 (e.g., which may include one or more processors) executes instructions of memory 1056 to provide some or all of the functionality described above as being provided by a UE with respect to AR-based assistance, e.g., generating appropriate assistance queries, interfacing with performance modules, environmental sensing, object recognition and spatial mapping (if integrated), presentation of AR/MR content in suitable forms (e.g., visual display, sound, etc.), and the like. Accordingly, suitable AR/MR gear and functionality 1060 and sensor elements 1062 may also be integrated within UE device 1000B. As noted elsewhere in the present disclosure, processing circuitry 1054 may include any suitable combination of hardware and software implemented in one or more modules to execute instructions and manipulate data to perform some or all of the foregoing functions. In some embodiments, processing circuitry 1054 may include, for example, one or more computers, one or more central processing units (CPUs), one or more microprocessors, one or more applications, one or more application specific integrated circuits (ASICs), one or more field programmable gate arrays (FPGAs) and/or other logic.

Other embodiments of wireless UE device 1000B may optionally include additional components beyond those shown in FIG. 10B that may be responsible for providing certain aspects of the wireless device's functionality, including any of the functionality described above and/or any additional functionality (including any functionality necessary to support one or more embodiments described above). As just one example, wireless UE device 1000B may include various types of input devices and circuits, output devices, and one or more synchronization units or circuits, which may be part of the processing circuitry 1054. Input devices include mechanisms for entry of data into wireless UE device 1000B in a number of modalities. For example, input devices may include a variety of input mechanisms, such as microphones, cameras, facial recognition, barcode/QR (Quick Response) code scanners, biometric input elements, displays, etc. Likewise, output devices may include mechanisms for outputting data in a variety of modalities, e.g., audio, video, and/or hard copy format, along with AR/MR-based sensory output.

Figure 11:
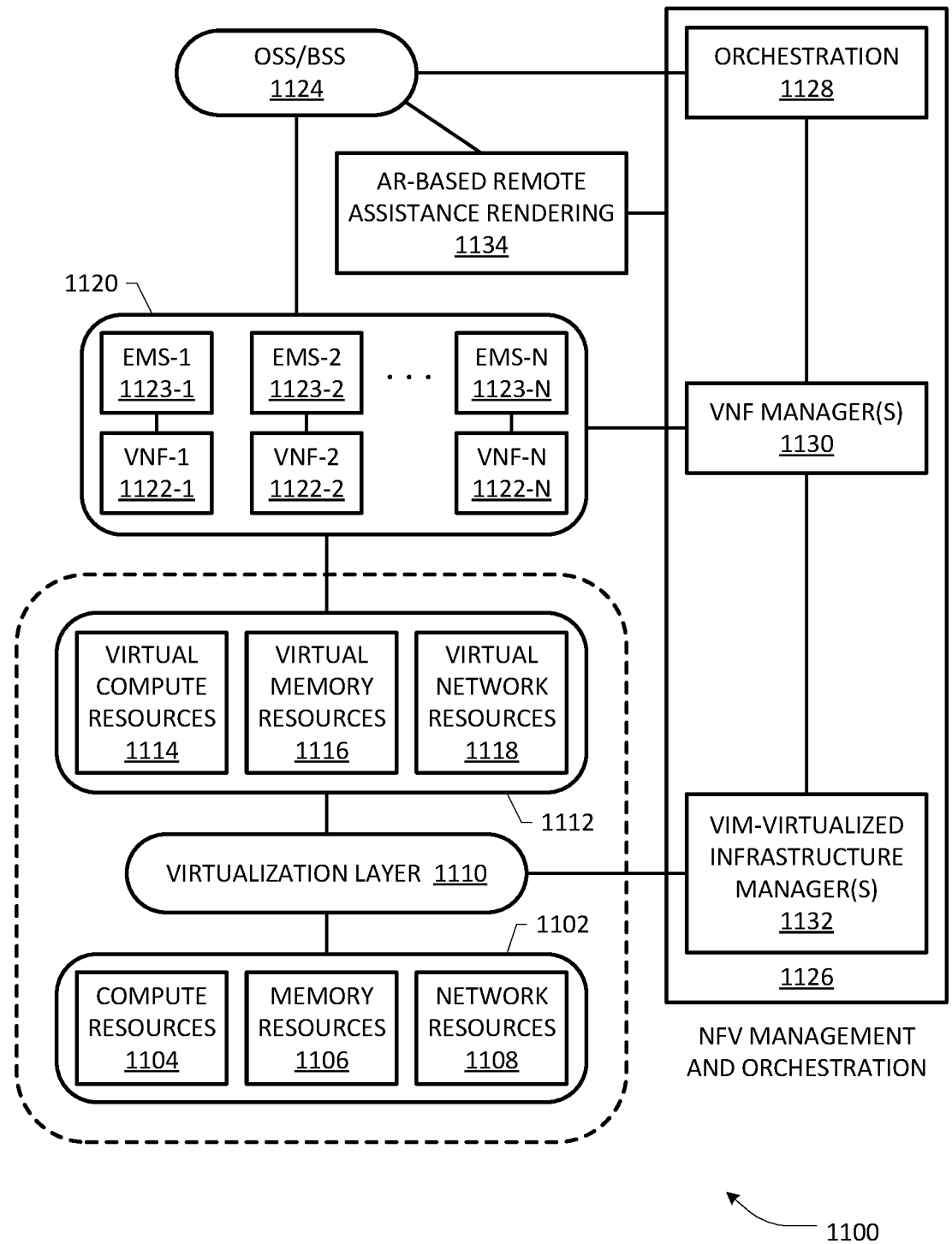
FIG. 11 depicts a Network Function Virtualization (NFV) architecture that may be implemented in conjunction with an ARRA platform according to an example embodiment of the present patent disclosure.

Turning to FIG. 11, depicted therein is a Network Function Virtualization (NFV) architecture 1100 that may be applied in conjunction with an ARRA platform of the present invention wherein a centralized or cloud-based implementation may be deployed (e.g., as depicted in FIG. 8). Various physical resources and services executing within a central network environment (e.g., involving one or more data centers) may be provided as virtual appliances wherein the resources and service functions are virtualized into suitable virtual network functions (VNFs) via a virtualization layer 1110. Resources 1102 comprising compute resources 1104, memory resources 1106, and network infrastructure resources 1108 are virtualized into corresponding virtual resources 1112 wherein virtual compute resources 1114, virtual memory resources 1116 and virtual network resources 1118 are collectively operative to support a VNF layer 1120 including a plurality of VNFs 1122-1 to 1122-N, which may be managed by respective element management systems (EMS) 1123-1 to 1123-N. Virtualization layer 1110 (also sometimes referred to as virtual machine monitor (VMM) or "hypervisor") together with the physical resources 1102 and virtual resources 1112 may be referred to as NFV infrastructure (NFVI) of a network environment. Overall NFV management and orchestration functionality 1126 may be supported by one or more virtualized infrastructure managers (VIMs) 1132, one or more VNF managers 1130 and an orchestrator 1128, wherein VIM 1132 and VNF managers 1130 are interfaced with NFVI layer and VNF layer, respectively. An Operation Support System (OSS) platform 1124 (which may be integrated or co-located with a Business Support System (BSS) in some arrangements) is responsible for network-level functionalities such as network management, fault management, configuration management, service management, and subscriber management, etc. In one arrangement, various OSS components of the OSS platform 1124 may interface with VNF layer 1120 and NFV orchestration 1128 via suitable interfaces. In addition, OSS/BSS 1124 may be interfaced with an AR-based remote assistance/optimization module 1134 for facilitating expert guidance generation, ML modeling of AR rendering, performance monitoring, etc. with respect to one or more work environments. Broadly, NFV orchestration 1128 involves generating, maintaining and tearing down of network services or service functions supported by corresponding VNFs, including creating end-to-end services over multiple VNFs in a network environment, (e.g., allocation of radio resources, baseband ports, etc.). Further, NFV orchestrator 1128 is also responsible for global resource management of NFVI resources, e.g., managing compute, storage and networking resources among multiple VIMs in the network.

Based on the foregoing, it should be appreciated that in the context of the present application, the AR-based remote assistance/optimization functionality associated with an OSS platform such as OSS 1124 may also be configured in an example embodiment to access or interface with suitable OSS components that may be mapped to different hierarchical information layers based on how the virtualized resources are organized in accordance with NFVI. Because the physical resources allocated to a VNF are considered to be elastic and the VNFs can run on multiple physical infrastructure network nodes, it should be appreciated that there is a loose coupling between the VNFs and the physical infrastructure hardware nodes they exist on, which allows greater scalability and dynamic configurability of a virtualized network environment. Consequently, the databases provided with different OSS components (based on the different hierarchical layers to which they are mapped) may need to be dynamically reconfigured as the underlying topologies change, e.g., depending on the scalability of the AR-based remote assistance/optimization platform.

Consistent with an NFV implementation, at least a portion of an example platform architecture disclosed herein may be virtualized as set forth above and architected in a cloud-computing environment comprising a shared pool of configurable virtual resources. Various pieces of hardware/software associated with AR rendering, ML modeling, ORS/SMaS data processing, guidance generation and contextualization, performance metrics, and the like, may be implemented in a service-oriented architecture, e.g., Software as a Service (SaaS), Platform as a Service (PaaS), infrastructure as a Service (IaaS) etc., with multiple entities providing different features of an example embodiment of the present invention, wherein one or more layers of virtualized environments may be instantiated on commercial off the shelf (COTS) hardware. Skilled artisans will also appreciate that such a cloud-computing environment may comprise one or more of private clouds, public clouds, hybrid clouds, community clouds, distributed clouds, multiclouds and interclouds (e.g., "cloud of clouds"), and the like.

Figure 12:
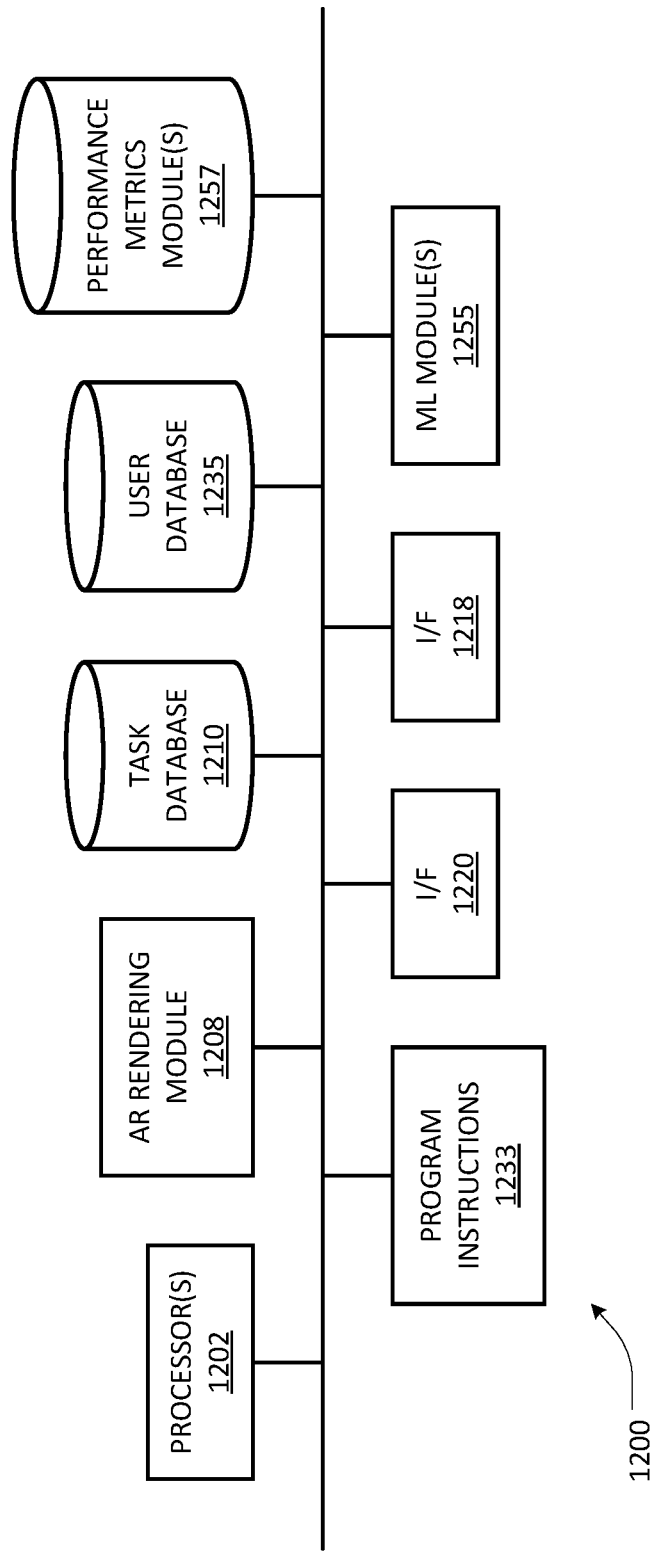
FIG. 12 depicts a block diagram involving a plurality of modules that may be configured as an integrated or distributed platform for effectuating AR-based remote assistance according to a further embodiment of the present patent disclosure.

FIG. 12 depicts a block diagram involving a plurality of modules that may be configured as an integrated or distributed platform 1200 for effectuating AR-based remote assistance according to a further embodiment of the present patent disclosure. In one arrangement, platform 1200 may be implemented as a computer-implemented apparatus that may be (re)configured and/or (re)arranged as a server, node or element, and the like to effectuate an example central network node or element having a more enhanced functionality than the embodiment shown in FIG. 9 set forth above. One or more processors 1202 may be operatively coupled to various modules that may be implemented in persistent memory for executing suitable program instructions or code portions (e.g., code portion 1233) with respect to effectuating AR-based remote assistance in association with one or more modules and databases, e.g., AR rendering module 1208, task database 1210, user/worker database 1235, as well as one or more ML modules 1255. One or more performance metrics modules 1257 may also be provided as part of the platform 1200. Although not specifically shown in this FIG., an embodiment of the platform 1200 may also optionally include a centralized object identification and spatial mapping module whose functionality may be configured depending on the work environment(s) with which the platform 1200 is associated. Accordingly, depending on the implementation, appropriate "upstream" interfaces (I/F) 1218 and/or "downstream" I/Fs 1220 may be provided for interfacing with external nodes or infrastructural elements, e.g., BSS nodes and/or other OSS components, network hubs, management nodes, micro/macro nodes, RRUs, macrocells, microcells, small cells, femtocells, picocells, etc., wherein such interfaces may be referred to as a first interface, a second interface, and so on.

Based on the foregoing, skilled artisans will appreciate that some embodiments herein may particularly leverage 5G network features to enable the assistance of less experienced workers by just a few remote experts using AR. Preferably, an example platform may be implemented as self-improving, that is, once it is online, it constantly improves in terms of (a) rendering the best AR view to assist the worker with a task; (b) assisting the worker by a non-human remote expert (bot); and (c) as a corollary effect of (b), supporting the "human" remote expert with the best response to a given situation.

It will be further realized that the example embodiments herein may be implemented in a broad range of practical applications. Although example task scenarios have been particularly illustrated in an industrial setting dealing with the rendering of a remote expert's directions on a specific task for an inexperienced worker using AR technologies, the disclosed systems and methods may be used in other domains, such as, e.g., a platform-based service for providing remote home handyman or remote car mechanics expert assistance. As just one example, a remote handyman could guide a person needing to change their dishwasher by using AR to perform the task, thereby reducing or eliminating the risk of accidents, etc. Furthermore, the platform may be configured to generate one or more properly trained AR-ML modules (e.g., equivalent to the ML Module 222) to eventually offer non-human bot assistants, wherein optimal AR rendering may be improved as the platform as well as the bot assistants are trained over a period of time.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. Such computer program instructions may be provided to a processor circuit of a general purpose computer circuit, special purpose computer circuit, and/or other programmable data processing circuit to produce a machine, so that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s). Additionally, the computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

As pointed out elsewhere in the present patent disclosure, tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-ray). The computer program instructions may also be loaded onto or otherwise downloaded to a computer and/or other programmable data processing apparatus to cause a series of operational steps to be performed on the computer and/or other programmable apparatus to produce a computer-implemented process. Accordingly, embodiments of the present invention may be embodied in hardware and/or in software (including firmware, resident software, micro-code, etc.) that runs on a processor or controller, which may collectively be referred to as "circuitry," "a module" or variants thereof. Further, an example processing unit may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine. As can be appreciated, an example processor unit may employ distributed processing in certain embodiments.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the scope of the claims appended below.

The invention claimed is:

1. A computer-implemented method, comprising:
receiving one or more guidance messages generated responsive to an assistance request provided by at least one requester with respect to a task to be performed by the at least one requester in a contextual setting;
constructing, responsive to the one or more guidance messages, a digital representation of a response to be taken by the at least one requester regarding the task, the digital representation based at least in part upon worker data pertaining to the at least one requester, the worker data including skill level data and capability data of the at least one requester; and
providing the digital representation of the response to the at least one requester for presentation via an augmented reality (AR) overlay in a user equipment (UE) device operated by the at least one requester to facilitate error reduction in performing the task,
wherein the construction of the digital representation is based at least in part upon rendering output received from a first machine learning (ML) module configured to facilitate an optimized AR rendering responsive to the worker data and contextual task data obtained with respect to the at least one requester, the task, and a learned pattern of rendering in one or more contexts similar to the contextual setting of the at least one requester, and the first ML module is dynamically trained responsive to a first set of data comprising feedback received from a human performance computation module (HPCM) configured to provide a performance metric relating to accuracy of the construction of digital representations of responses, and
wherein the one or more guidance messages are generated based at least in part upon output received from a second ML module responsive to task performance and completion data relating to the at least one requester, the task, and a learned pattern of the task performance and completion data in the one or more contexts similar to the contextual setting of the at least one requester, the second ML module dynamically trained responsive to a second set of data comprising feedback received from a task performance computation module (TPCM) configured to provide a performance metric relating to how well tasks are performed.

2. The computer-implemented method as recited in claim 1, wherein the first ML module is configured to obtain the learned pattern of rendering in the one or more contexts similar to the contextual setting of the at least one requester in a trainable manner.

3. The computer-implemented method as recited in claim 1, wherein the second ML module is configured to obtain the learned pattern of the task performance and completion data in the one or more contexts similar to the contextual setting of the at least one requester in a trainable manner.

4. The computer-implemented method as recited in claim 1, further comprising interacting with the at least one requester via a query-response mechanism to improve the digital representation of the response for facilitating a more accurate AR rendering.

5. The computer-implemented method as recited in claim 1, wherein the digital representation of the response corresponds to at least one of an audio component, a video component, a multimedia component, and a sensory data component.

6. The computer-implemented method as recited in claim 1, further comprising training at least one of the first ML module and the second ML module using a simulated contextual setting with respect to the task, the training taking place prior to providing any guidance messages to the at least one requester.

7. A non-transitory computer-readable medium comprising instructions which, when executed on a computer platform, perform a method comprising: receiving one or more guidance messages generated responsive to an assistance request provided by at least one requester with respect to a task to be performed by the at least one requester in a contextual setting; constructing, responsive to the one or more guidance messages, a digital representation of a response to be taken by the at least one requester regarding the task, the digital representation based at least in part upon worker data pertaining to the at least one requester, the worker data including skill level data and capability data of the at least one requester; and providing the digital representation of the response to the at least one requester for presentation via an augmented reality (AR) overlay in a user equipment (UE) device operated by the at least one requester to facilitate error reduction in performing the task, wherein the construction of the digital representation is based at least in part upon rendering output received from a first machine learning (ML) module configured to facilitate an optimized AR rendering responsive to the worker data and contextual task data obtained with respect to the at least one requester, the task, and a learned pattern of rendering in one or more contexts similar to the contextual setting of the at least one requester, and the first ML module is dynamically trained responsive to a first set of data comprising feedback received from a human performance computation module (HPCM) configured to provide a performance metric relating to accuracy of the construction of digital representations of responses, and wherein the one or more guidance messages are generated based at least in part upon output received from a second ML module responsive to task performance and completion data relating to the at least one requester, the task, and a learned pattern of the task performance and completion data in the one or more contexts similar to the contextual setting of the at least one requester, the second ML module dynamically trained responsive to a second set of data comprising feedback received from a task performance computation module (TPCM) configured to provide a performance metric relating to how well tasks are performed.

8. The non-transitory computer-readable medium as recited in claim 7, wherein the first ML module is configured to obtain the learned pattern of rendering in the one or more contexts similar to the contextual setting of the at least one requester in a trainable manner.

9. The non-transitory computer-readable medium as recited in claim 7, wherein the second ML module is configured to obtain the learned pattern of the task performance and completion data in the one or more contexts similar to the contextual setting of the at least one requester in a trainable manner.

10. The non-transitory computer-readable medium as recited in claim 7, further comprising interacting with the at least one requester via a query-response mechanism to improve the digital representation of the response for facilitating a more accurate AR rendering.

11. The non-transitory computer-readable medium as recited in claim 7, wherein the digital representation of the response corresponds to at least one of an audio component, a video component, a multimedia component, and a sensory data component.

12. The non-transitory computer-readable medium as recited in claim 7, further comprising training at least one of the first ML module and the second ML module using a simulated contextual setting with respect to the task, the training taking place prior to providing any guidance messages to the at least one requester.

13. An apparatus comprising processing circuitry and a non-transitory computer readable medium storing program instructions which, when executed by the processing circuitry, perform a method comprising:
    receiving one or more guidance messages generated responsive to an assistance request provided by at least one requester with respect to a task to be performed by the at least one requester in a contextual setting;
    constructing, responsive to the one or more guidance messages, a digital representation of a response to be taken by the at least one requester regarding the task, the digital representation based at least in part upon worker data pertaining to the at least one requester, the worker data including skill level data and capability data of the at least one requester; and
    providing the digital representation of the response to the at least one requester for presentation via an augmented reality (AR) overlay in a user equipment (UE) device operated by the at least one requester to facilitate error reduction in performing the task,
    wherein the construction of the digital representation is based at least in part upon rendering output received from a first machine learning (ML) module configured to facilitate an optimized AR rendering responsive to the worker data and contextual task data obtained with respect to the at least one requester, the task, and a learned pattern of rendering in one or more contexts similar to the contextual setting of the at least one requester, and the first ML module is dynamically trained responsive to a first set of data comprising feedback received from a human performance computation module (HPCM) configured to provide a performance metric relating to accuracy of the construction of digital representations of responses, and
    wherein the one or more guidance messages are generated based at least in part upon output received from a second ML module responsive to task performance and completion data relating to the at least one requester, the task, and a learned pattern of the task performance and completion data in the one or more contexts similar to the contextual setting of the at least one requester, the second ML module dynamically trained responsive to a second set of data comprising feedback received from a task performance computation module (TPCM) configured to provide a performance metric relating to how well tasks are performed.

14. The apparatus as recited in claim 13, wherein the first ML module is configured to obtain the learned pattern of rendering in the one or more contexts similar to the contextual setting of the at least one requester in a trainable manner.

15. The apparatus as recited in claim 13, wherein the second ML module is configured to obtain the learned pattern of the task performance and completion data in the one or more contexts similar to the contextual setting of the at least one requester in a trainable manner.

16. The apparatus as recited in claim 13, further comprising interacting with the at least one requester via a query-response mechanism to improve the digital representation of the response for facilitating a more accurate AR rendering.

17. The apparatus as recited in claim 13, wherein the digital representation of the response corresponds to at least one of an audio component, a video component, a multimedia component, and a sensory data component.

18. The apparatus as recited in claim 13, further comprising training at least one of the first ML module and the second ML module using a simulated contextual setting with respect to the task, the training taking place prior to providing any guidance messages to the at least one requester.

* * * * *